US008236283B2

(12) United States Patent
Cuthbertson et al.

(10) Patent No.: US 8,236,283 B2
(45) Date of Patent: *Aug. 7, 2012

(54) OPTICAL IMAGING

(75) Inventors: Alan Cuthbertson, Oslo (NO); Maria E. Verdugo-Gazdik, Irvine, CA (US)

(73) Assignee: GE Healthcare AS, Oslo (NO)

( * ) Notice: Subject to any disclaimer, the term of this patent is extended or adjusted under 35 U.S.C. 154(b) by 1132 days.

This patent is subject to a terminal disclaimer.

(21) Appl. No.: 11/813,445

(22) PCT Filed: Jan. 6, 2006

(86) PCT No.: PCT/NO2006/000005
§ 371 (c)(1),
(2), (4) Date: May 2, 2008

(87) PCT Pub. No.: WO2006/073314
PCT Pub. Date: Jul. 13, 2006

(65) Prior Publication Data
US 2009/0232741 A1 Sep. 17, 2009

Related U.S. Application Data

(60) Provisional application No. 60/642,289, filed on Jan. 6, 2005.

(51) Int. Cl.
*A61K 49/00* (2006.01)

(52) U.S. Cl. ....... 424/9.1; 424/1.11; 424/1.65; 424/1.69

(58) Field of Classification Search ............... 424/1.11, 424/1.49, 1.65, 1.69, 1.73, 1.81, 1.85, 1.89, 424/9.1, 9.2, 9.3, 9.4, 9.5, 9.6, 9.7, 9.8; 514/1, 514/1.11, 21.1, 21.3, 21.4, 21.5, 21.6, 21.7, 514/21.8, 21.9; 530/300, 316, 317, 323, 530/324, 325, 326, 327, 328, 329, 330, 331
See application file for complete search history.

(56) References Cited

U.S. PATENT DOCUMENTS

| 6,852,318 | B1 * | 2/2005 | Varner ................... 424/130.1 |
| 6,943,153 | B1 * | 9/2005 | Manning et al. ............ 514/44 R |
| 7,351,790 | B2 * | 4/2008 | Cuthbertson et al. ......... 530/317 |
| 7,608,243 | B2 * | 10/2009 | Cuthbertson et al. ........ 424/1.69 |
| 2003/0045681 | A1 * | 3/2003 | Neri et al. ..................... 530/350 |
| 2003/0113320 | A1 * | 6/2003 | Ruoslahti et al. .......... 424/143.1 |

FOREIGN PATENT DOCUMENTS

| EP | 1325932 | * | 7/2003 |
| EP | 1 110 963 | | 4/2004 |
| WO | WO 01/77145 | * | 10/2001 |
| WO | WO 02/26776 | | 4/2002 |
| WO | WO 02/30473 | | 4/2002 |
| WO | WO 2004/058802 | | 7/2004 |
| WO | WO 2004/058803 | | 7/2004 |
| WO | WO 2005/003166 | * | 1/2005 |

OTHER PUBLICATIONS

Kulkarni et al (Advanced Drug Delivery Reviews, Amsterdam, 2005, vol. 57, No. 14, pp. 1994-2009).*

* cited by examiner

*Primary Examiner* — D L Jones

(57) ABSTRACT

This invention relates to a method for imaging of wet age-related macular degeneration (AMD) using a contrast agent comprising a vector attached to an optical imaging reporter, wherein the vector has affinity for receptors associated with angiogenesis. The invention further provides such methods for monitoring the effect of treatment of AMD.

6 Claims, 1 Drawing Sheet

OPTICAL IMAGING

This application is a filing under 35 U.S.C. 371 of international application number PCT/NO2006/000005, filed Jan. 6, 2006, which claims priority to application No. 60/642,289 filed Jan. 6, 2005, in the United States the entire disclosure of which is hereby incorporated by reference.

FIELD OF THE INVENTION

This invention relates to a method of imaging of wet age-related macular degeneration (AMD) using a contrast agent comprising a vector attached to an optical imaging reporter, wherein the vector has affinity for receptors associated with angiogenesis. The invention further provides such methods for monitoring the effect of treatment of AMD.

BACKGROUND OF INVENTION

Age-related macular degeneration (AMD) is a retinal degenerative disease that causes progressive loss of central vision. The risk of developing AMD increases with age and most often affects people in their sixties and seventies or older. AMD is the leading cause of legal blindness in the developed world in patients over the age of sixty-five, and it ranks second, after diabetic retinopathy, between age 45 and 65.

Central vision loss from AMD is caused by photoreceptor degeneration in the macula region. The macula region is the central portion of the fundus and retina, responsible for perceiving fine visual details and the macula region has the highest photoreceptor density of the eye. The fundus is the posterior ½-⅓ part of the eye and contains the same three tissue layers as the rest of the eye, retina, chorioid and sclera (anterior to posterior). Light sensing cells in the retina, known as photoreceptor cells, convert light into electrical impulses and then transfer these impulses to the brain via the optic nerve.

The following abbreviations are used throughout the text:

| | |
|---|---|
| AMD | Age-related macular degeneration |
| CCD | Charge coupled device |
| CNV | Choroidal neovascularization |
| ICG | Indocyanine green |
| NIR | Near infrared |
| PDT | Photodynamic therapy |
| RGD | Arginine-glycine-aspartic acid |
| RPE | Retinal pigment epithelium |
| SLO | Scanning laser ophthalmoscopy |
| VEGF | Vascular endothelial growth factor |

There are two types of AMD: dry and wet. Dry AMD is also called atrophic, nonexudative, or drusenoid macular degeneration. With dry AMD, yellow-white deposits called drusen accumulate between the retinal pigment epithelium (RPE) tissue and Bruch's membrane as a result of accumulated retinal waste. Drusen deposits are visible in white and fluorescent light fundus imaging and no contrast agent is required for diagnosis. Drusen deposits are composed of waste products from photoreceptor cells, which are not handled correctly by the RPE. The RPE cells normally act as "gatekeepers", supplying nutrients to and scavenging waste products from the photoreceptors across Bruch's membrane. The drusen deposits, which occur in as well as outside the macula region, are thought to interfere with the normal function and maintenance of photoreceptors, causing progressive degeneration of these cells. Drusen deposits can, however, be present in the retina for many years without vision loss. Vision loss from dry AMD occurs very gradually over the course of many years.

Wet AMD is characterised by the presence of choroidal neovascularization (CNV) and neovascular membranes, and is also called subretinal neovascularization, exudative, or disciform degeneration, in addition to CNV. In wet AMD, abnormal new blood vessels originate in the choroid and penetrate through Bruch's membrane. When these new or "angiogenic" vessels are located posterior to the RPE, a so called type I or "occult type" AMD is formed. When the new vessels are located anterior to the RPE, a so called type II or "classic type" AMD is formed. Combinations of type I and II also occur. These new vessels and the proliferative RPE response form "neovascular membranes", which leak blood and fluid into the subretinal cells. The neovascular membranes are leaky because the fenestrations between the endothelial linings of angiogenic vessels are wider than in normal vessels and allow extravasation of macromolecular substances (plasma and blood). The process of new vessel formation, as well as the blood and fluid leakage, damage the photoreceptor cells and further compromise the RPE support of the photoreceptors. Current methods of AMD diagnosis with fluorescein and indocyanine green (ICG) rely on the leaky nature of angiogenic vessels and hence focal accumulation of the fluorophores due to this morphological/structural abnormality. Diagnosis of AMD is therefore today only possible at relatively advanced stages of AMD, when sufficient neovascular membranes have formed. Due to the relatively late diagnosis with the diagnostic agents available today, wet AMD therefore tends to progress rapidly and carries the highest risk of severe impairment to vision. In a majority of patients with wet AMD occult lesions are present particularly during the initial stages of AMD. Despite the above knowledge about AMD pathology, many aspects and mechanism of CNV are not well understood.

In the USA today there are about 15 million people having AMD, 90% having the dry type and 10% having the wet type. It has been estimated that there will be 2 million new cases per year in the USA in the future.

Generally, new blood vessels can be formed by two different mechanisms: vasculogenesis or angiogenesis. Angiogenesis is the formation of new blood vessels by branching from existing vessels and occurs as a normal event in embryologic development and health, as well as part of various disease processes. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis involves receptors that are unique to endothelial cells and surrounding tissues. These angiogenesis receptors include growth factor receptors such as VEGF and the integrin receptors. Immunohistochemical studies have demonstrated that a variety of integrins, perhaps most importantly the $\alpha_v$ class, are expressed on the apical surface of blood vessels [Conforti, G., et al. (1992) Blood 80: 37-446] and are available for targeting by circulating ligands [Pasqualini, R., et al. (1997) Nature Biotechnology 15: 542-546].

The integrins $\alpha v \beta_3$ and $\alpha v \beta 5$ are receptors known to be associated with angiogenesis. Stimulated endothelial cells appear to rely on these receptors for survival during a critical period of the angiogeneic process, as antagonists of the $\alpha v \beta_3$ integrin receptor/ligand interaction induce apoptosis and inhibit blood vessel growth.

Integrins are heterodimeric molecules in which the $\alpha$- and $\beta$-subunits penetrate the cell-membrane lipid bilayer. The $\alpha$-subunit has four $Ca^{2+}$ binding domains on its extracellular chain, and the $\beta$-subunit has a number of extracellular cysteine-rich domains.

Many ligands (e.g. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. Perhaps the most widely studied effect of RGD peptides and mimetics thereof relate to their use as anti-thrombotic agents where they target the platelet integrin GpIIbIIIa.

Examples of RGD-containing peptide-based contrast agents are found in WO 01/77145, WO 02/26776 and WO 03/006491.

In some cases, if wet AMD is diagnosed early, laser surgery (photocoagulation) can prevent extensive central vision loss. In this type of surgery, laser beams cauterise the leaky blood vessels of the neovascular membranes. For laser surgery to be effective, it is critical that wet AMD is diagnosed before extensive vision loss occurs.

Another treatment for wet AMD is photodynamic therapy (PDT). PDT uses a light sensitive drug (e.g. Visudyne™; liposomal BPD-MA verteporfin) in combination with laser treatment. Administered intravenously, the photosensitive drug is inactive and accumulates in the undesired neovascular membranes. A predetermined amount of low-energy laser light is delivered to the target CNV tissue, which activates the drug contained within the vessels. The laser light, when combined with the photosensitive drug, invokes a highly reactive form of oxygen in the target tissue that leads to closure of the unwanted blood vessels. PDT therapy is highly selective and involves low-level, non-thermal laser energy, minimizing damage to the surrounding retinal tissue. The entire procedure can be accomplished in approximately 30 minutes and is performed on an outpatient basis. Typically, the new blood vessels remain closed for a few weeks or months, after which a re-treatment may be necessary. There is hence a need for methods to diagnose wet AMD and to monitor the treatment of the indication.

The existing methods for detection of wet AMD is by angiography with a fundus camera during intravenous administration of fluorescein and/or ICG. The diagnostic principle for both agents is detection of vascular morphological/structural changes, leading to leakage from angiogenic vessels and requiring relatively high dosages to obtain bolus passage and sufficient tissue concentrations after systemic distribution. After a short arterial and venous bolus phase upon intravenous administration, fluorescein extravasates and distributes relatively rapid in the extracellular fluid space. A diffuse and dominating fluorescence signal from the choroidal vasculature is therefore observed from 20-30 seconds after administration of fluorescein (without any anatomical resolution). Angiogenic vessels are hence distinguished by "excessive" neovascular membranes and present as locally increased fluorescence. Leakage of fluorescein in classic type AMD is easier to diagnose (located anterior to the RPE) and shows well-demarcated areas of hyperfluorescence and homogeneous leakage. As indicated by its name, occult type AMD is more difficult to diagnose with fluorescein, as the RPE act as a very effective optical barrier to both excitation and emission light. Use of fluorescein is therefore not reliable for occult type AMD, although irregular fluorescence ("stippling") in the early phase and inhomogeneous leakage at the late phase is observed in some cases. Analysis of fluorescein angiograms can yield haemodynamic information such as arteriovenous passage time and mean dye velocity. U.S. Pat. No. 6,599,891 is one of many examples disclosing methods of PDT and imaging using fluorescein angiography.

ICG binds very strongly to albumin and hence behaves more or less like a blood pool tracer. The maximum excitation and emission wave lengths of ICG are 806 nm and 830 nm, respectively, resulting in relatively little absorption by the RPE. The RPE light absorption is dependent upon the wavelength and is the least in the near-infrared range. ICG does hence confer angiographic details from the choroidal tissue and tissues posterior to the RPE layer, which is of importance in cases of occult type AMD. However, as with fluorescein, vascular morphological/structural changes and passive leakage is the diagnostic principle with ICG and only well advanced focal neovascular membranes can therefore be diagnosed with ICG. US2004/0156782 discloses a method of using ICG for obtaining angiographic images of CNV.

Neither fluorescein nor ICG angiography provide methods for detection of wet AMD in early phases, before substantial volumes of neovascular membranes have formed and visual impairment has started.

WO 2004/034889 discloses methods, apparatus and systems for the photodynamic treatment of feeder vessels associated with choroidal neovasculature, and also describes the need for detection of such feeder vessels. The therapy method includes using a photosensitizer with may be coupled to a binding ligand which binds to a specific surface component of the target ocular tissue. To detect the feeder vessels conventional fluoroescein angiography and ICG angiography are suggested used.

There is a clinical need to develop more specific non-invasive imaging techniques for AMD, and particularly for wet AMD and occult choroidal neovascularisation. The existing techniques do not diagnose the underlying pathology, but only identify morpholocal/structural changes by leaky angiogenic vessels when the formation and volume of neovascular membranes is well advanced. As the relatively poor prognosis of wet AMD is among other due to the relatively late diagnosis provided with the currently available methods, new imaging methods with the ability to diagnose smaller and earlier lesions and preferably the nature of the underlying pathology will be of clinical benefit in diagnosing and monitoring the development of AMD at an early stage. Such imaging methods will also have a central role in the evaluation of novel anti-angiogenic therapies.

SUMMARY OF THE INVENTION

The present invention provides a method of imaging of wet AMD using a contrast agent comprising a vector attached to an optical imaging reporter, wherein the vector has affinity for receptors associated with angiogenesis. The detection of angiogenesis, which is the pathological basis of neovascular membrane formation, has been found to be an earlier diagnostic indicator for wet AMD than monitoring indirect signs such as leakage of already well established pathology. The efficient targeting and imaging of receptors associated with angiogenesis and wet AMD in vivo demands a selective, high affinity vector that is chemically robust and stable. It has been found that using a contrast agent as described has added value over traditional angiography as it provides cellular receptor information about the early pathology development specifically related to angiogenesis.

DETAILED DESCRIPTION OF THE INVENTION

Figure 1:
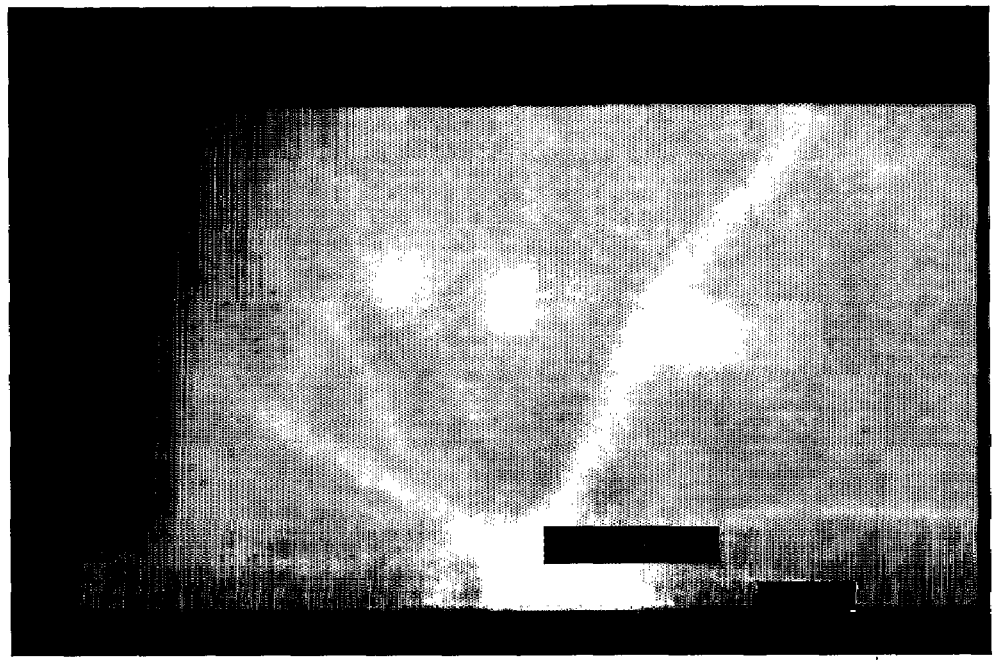
FIG. 1 shows an image of a representative rat eye injected with contrast agent H, showing an increased intensity of signal for the induced lesions.

Viewed from a first aspect the invention provides a method of imaging of wet AMD of a human or animal body, using a contrast agent comprising a vector attached to an optical imaging reporter wherein the vector has affinity for receptors associated with angiogenesis.

The method preferably comprises generating an image of an eye, or part of an eye, of a human or animal body by optical imaging involving administering the contrast agent to said body, irradiating the eye or part of the eye with light and generating an image of the eye, or part of the eye, to which said contrast agent has distributed. The fundus of the eye is the preferred part of the eye which is irradiated and of which an image is generated. The method of imaging may be used for detection and/or diagnosis of wet AMD in both humans and animals and in animal models e.g. as used in pre-clinical studies.

The contrast agent is preferably administrated into the vascular system of the human or animal body by an intravenous injection. The administered dose is expected to be lower than used for fluorescein and indocyanine green angiography. A typical dose is preferably of 1 to 100 nmol/kg.

Said method preferably involves detecting the accumulation of said contrast agent by cell receptors, preferably endothelial cell receptors and in particular the integrin receptors $\alpha v \beta 3$ and/or $\alpha v \beta 5$. By accumulation is meant that the contrast agent binds to, associates with or is taken up by receptors associated with angiogenesis.

To generate an image of wet AMD, the eye, or part of an eye, is irradiated with light, preferably having a wavelength of 400-1300 nm, and more preferably of 600-800 nm. A fluorescence image is generated by detection of the emitted fluorescence. The generation of an image hence constitutes an examination phase involving the collection of data. The contrast agent is preferably highly fluorescent absorbing light within one wavelength range and emitting fluorescence at a range with a longer wavelength. Filters are conveniently used to separate the emission from the excitation light and images of the emitted light are generated.

In a further embodiment, the method includes use of optical imaging techniques wherein images are formed based on interaction with light in the electromagnetic spectrum from ultraviolet to near-infrared radiation, falling within the term optical imaging. Some contrast agents, for use in the method, emit in the visual range of the spectrum and conventional opthalmoscopy equipment may then be used for generating the images. Fluorescence images can also be recorded using a confocal scanning laser opthalmoscope (SLO) which is a more sensitive type of fundus camera and which allows for quantitative angiography. Furthermore, in-vivo confocal microscopy may be applied. Recently developed time-domain and frequency-domain imaging techniques may also be used, taking advantage of additional characteristics of the reporter, such as lifetime. Preferably, a specialized fundus camera capturing sequence photographs of fluorescence following the administration of the contrast agent is used. More preferably a specialized fundus camera is used equipped with a matched pair of exciter and barrier filters along with a pulse light source, and preferably a sensitive light detection system (camera) allowing a capture rate of up to one frame per second. Inclusion of narrow band-pass interference filters are preferred to allow maximum transmission of peak wavelengths, while minimizing any crossover of transmission curves. The barrier filter effectively blocks the excitation light but not the specific colour of the emitted fluorescence. Fundus cameras equipped for angiography preferably have a timer that records the angiographic sequencing on each frame of the study. Images are captured electronically, with a sensitive charge-coupled device (CCD) and computerized system for digital imaging.

A sequencing of the fluorescence series generated is preferred for obtaining maximum diagnostic information. In a preferred embodiment, colour fundus photographs as well as monochromatic images at excitation light are taken as baseline views before administering the contrast agent. Images are preferably taken at different time points for an optimal evaluation of the area of interest. An early stage of the image generation facilitates the in-vivo study of the retinal and choroidal circulation while the later stage of the image generation provides visualisation of the contrast agent accumulation. The late or elimination phase demonstrates the gradual elimination of contrast agent from the retinal and choroidal vasculature. Staining of areas of late hyperfluorescence suggests the presence of an abnormality being imaged.

The method includes detection and/or diagnosis of wet AMD by generating images of the angiogenesis in the eye of a body. Preferably the method includes an assessment of the level of angiogenesis in an eye, or part of an eye, of a human or animal body for detection or diagnosis of wet AMD. The amount or presence of new blood vessels formed is detected by use of the method, such as new blood vessels in the choroids and those which have penetrated the Bruch's membrane. Both new vessels which are located anterior to the retinal pigment epithelium (RPE), i.e. classical AMD, and posterior to the RPE, i.e. occult AMD, can be detected. A method according to the invention for detection or diagnosis of occult CNV, i.e. occult AMD, is a preferred embodiment.

Further, by using the method of the invention information at molecular level related to pathological processes can be obtained. In a preferred embodiment the method of imaging provides cellular receptor information about the early pathology development specifically related to angiogenesis.

The method of the invention enables detection of smaller lesions and enables detection of wet AMD in early phases of the disease, before substantial volumes of neovascular membranes have formed and visual impairment has started.

In one embodiment, the method of the invention includes follow up of disease development or follow up of disease treatment. Thus, the invention provides a method of monitoring the effect of treatment of a human or animal body with a drug to combat wet AMD, such as monitoring the therapy response to angiogenesis inhibitors. The administration and detection is preferably being effected repeatedly, e.g. before, during and after treatment with said drug. In a preferred embodiment, the method of imaging is used in combination with photodynamic therapy. This method provides access to an early non-invasive and imaging tool as a surrogate endpoint for therapeutic efficacy of potential drugs for AMD, with associated benefits later in clinical trial design.

The invention further includes the following aspects, which all encompass the same embodiments as disclosed for the first aspect.

A preferred aspect of the invention is contrast agents comprising a vector attached to an optical imaging reporter wherein the vector has affinity to receptors associated with angiogenesis for use in optical imaging of wet AMD. The use may include detection or diagnosing of wet AMD in both humans and animals or in animal models, and also allows for monitoring of therapeutic efficacy of new drugs within pharmaceutical research.

Viewed from a further aspect the invention provides the use of a contrast agent comprising a vector attached to an optical imaging reporter, wherein the vector has affinity for receptors associated with angiogenesis, for the manufacture of a contrast enhancing composition for use in imaging of wet AMD. The imaging preferably involves administration of said contrast enhancing composition to a human or animal body and generation of an image of an eye, or a part of an eye, of the body, by optical imaging.

Viewed from a further aspect the invention provides a method of generating images of a wet AMD of the eye of a human or animal body previously administered with a contrast agent comprising a vector attached to an optical imaging reporter, wherein the vector has affinity for receptors associated with angiogenesis.

The present invention also provides methods and use for imaging of wet AMD using contrast enhancing compositions comprising an effective amount, e.g. an amount effective for enhancing image contrast in in vivo imaging, of a contrast agent comprising a vector attached to an optical imaging reporter or a salt thereof, together with one or more pharmaceutically acceptable adjuvants, excipients or diluents. The vector has affinity for receptors associated with angiogenesis.

The contrast agents used in the method of the invention, or physiologically acceptable salts thereof, comprise a vector attached to at least one optical imaging reporter, wherein the vector has affinity for receptors associated with angiogenesis. The contrast agents have affinity for receptors selected from the group consisting of vascular endothelial growth factor (VEGF) receptors, of which there are the following subtypes VEGFR-1/Flt-1, VEGFR-2/Flk-1/KDR, VEGFR-3/Flt-4; Placenta growth factor receptors and receptors for Fibroblast growth factors; Platelet derived endothelial cell growth factors; angiopoietins and integrins. Associated vectors with affinity for any of the above receptor classes are considered useful in relation to this invention when attached to an optical imaging reporter. Contrast agents comprising vectors with affinity for Integrins are preferred. By the term "attached" is meant that the reporter and vector are linked or coupled to each other, by a chemical bond, either directly or via a linker.

Preferably the vectors of the contrast agents have affinity for the integrin receptors αvβ3 and/or αvβ5. The vector is preferably a peptidic vector, and comprises the amino acid sequence $X_3$-G-D, such that the contrast agents preferably comprise said peptidic vector coupled to the optical imaging reporter, preferably by a covalent bond. $X_3$ represents arginine, N-methylarginine or an arginine mimetic, G represents glycine and D represents aspartic acid. The peptidic vector has affinity for integrin receptors, such as the αvβ3 receptors. The contrast agent preferably comprises further amino acids, and optionally other moieties, wherein the $X_3$-G-D sequence is the binding seat of the peptidic vector which functions as a vector binding to an integrin type receptor associated with angiogenesis and AMD.

Other relevant vectors which have been shown to inhibit the process of angiogenesis and which are considered specific enough as vectors for the contrast agents of this invention include the peptides angiostatin, endostatin, vasostatin and cleavage products of platelet factor 4 and anti-thrombin III.

Also considered useful are vectors derived from small molecule of non-peptide mimetics of the RGD (arginine-glycine-aspartic acid) tripeptide sequence, preferable the isoxazolines, indazoles, 2-benzazepine RGD mimetics and non-peptide azacarba-derivatives. Further relevant vectors are disclosed in WO 98/47541.

Examples of such vectors derived from small molecules of non-peptide mimetics of the RGD are shown below:

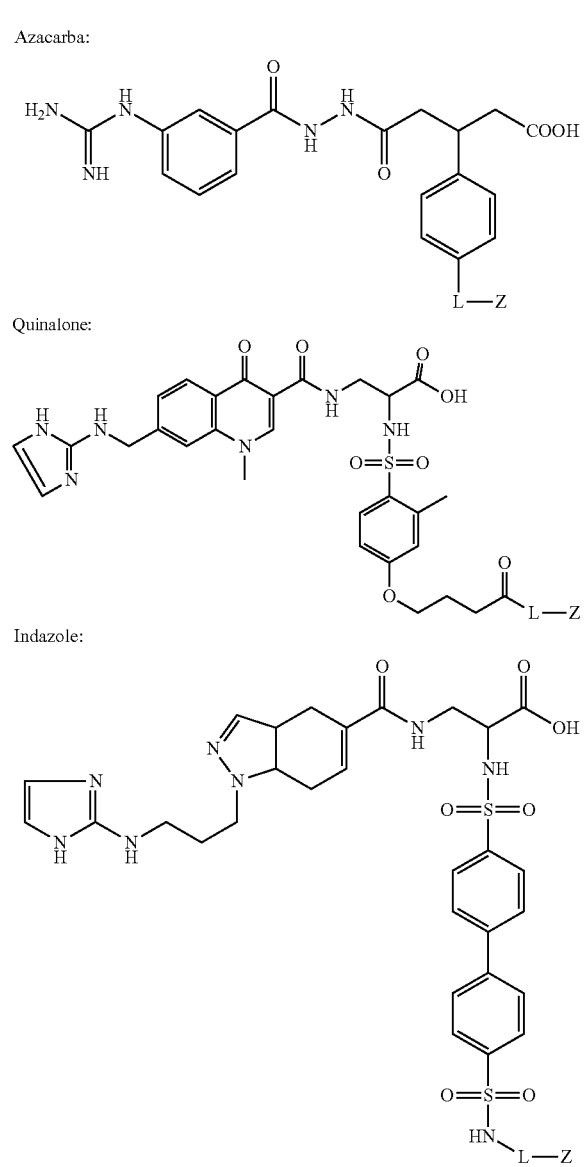

where L is a linker such as one or more amino acids, preferably carrying a positive or negative charge such as lysine or cysteic acid or is a spacer comprising multiple ethylene glycol units, or is a covalent bond and Z is an optical imaging reporter.

The optical imaging reporter is in the following represented by the letter Z. Z is preferably a fluorescent dye. The reporter fluoresces at certain wavelengths and has extensive conjugated electron systems. Reporters that emit radiation in the visible and near infrared (NIR) spectrum are preferred, and NIR-emitting reporters are most preferred. The optical imaging reporter is preferably little affected by RPE light absorption. The reporter Z is preferably selected from the group consisting of cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes and bis(S,O-dithiolene) complexes. More preferably, Z is fluorescein or a fluorescein derivative, or a cyanine dye, and most preferably Z is a cyanine dye. An alternative group of reporters is quantum dots.

Cyanine dyes (CyDye™) are compounds defined by a polyene chain containing an odd number of carbon atoms linked by alternating single and multiple, preferably double, carbon-carbon bonds, terminated at either end by an amino group, one of which is quaternised. The cyanine and analogues aryl-linker-aryl chromophores optionally carry pendant or fused ring substituents. General description of cyanine dyes and synthesis thereof are described in U.S. Pat. No. 6,048,982 and U.S. Pat. No. 5,268,486 which are hereby incorporated by reference. The cyanine dyes are particularly useful due to the wide range of spectral properties and structural variations available. A range of cyanine dyes are well known and tested, they have low toxicity, and are commercially available (GE Healthcare, formerly Amersham Biosciences). The cyanine dyes are a single family of highly intense dyes with good aqueous solubility. They are pH insensitive between pH 3-10, exhibit low non-specific binding, and are more photostable than fluorescein.

The cyanine dye is preferably selected from the groups consisting of carbacyanines, oxacyanines, thiacyanines and azacyanines shown below by general formulas.

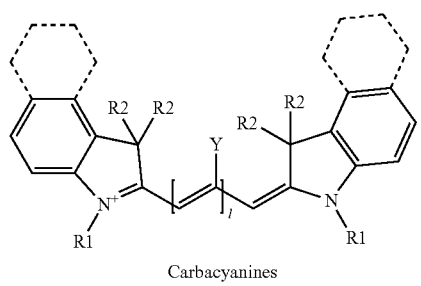

Carbacyanines

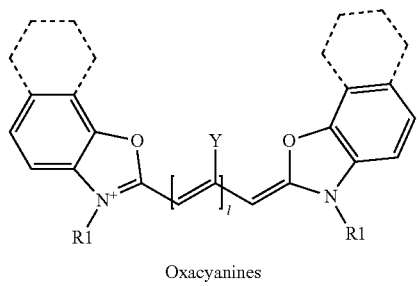

Oxacyanines

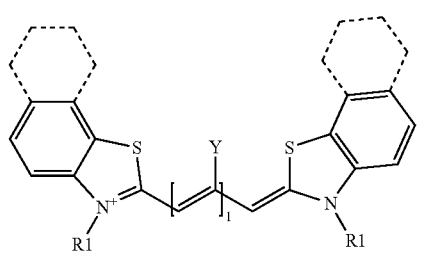

Thiacyanines

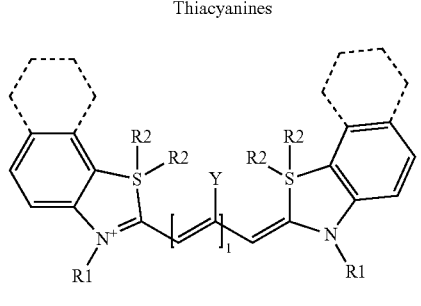

Azacyanines

In these structures the R1-groups are the same or different and are substituted or unsubstituted alkyl groups, preferably C1 to C6 alkyls, and may comprise an ether or an —N—CO—N— group. The alkyl groups are optionally substituted with carboxy, sulphonic acid, amine, ammonium or ester groups. The R1-groups may form bridges with any of the carbon-atoms of the polyene chains, e.g. by a —N—CO—N— group or an ether-group. The R2-groups are also the same or different and are substituted or unsubstituted alkyl groups. The alkyl groups are optionally substituted with carboxy or sulphonic acid groups, but preferably the R2-groups are lower alkyl groups, such as C1 to C6 alkyls, and most preferably methyl groups. Optional aromatic groups are indicated by dotted lines, to cover both structures comprising condensed benzo rings and condensed naphtho rings. The rings are substituted or unsubstituted. The rings may be substituted with sulphonic acid groups, carboxylic groups, hydroxyl groups, alkyl(sulphoalkyl)amino groups, bis(sulphoalkyl)amino groups, sulphoalkoxy groups, sulphoalkylsulphonyl group, alkyl or substituted alkyl or sulphoalkylamino groups. The alkyl-groups are preferably lower alkyls with e.g. 1 to 6 carbon atoms. Y is selected from hydrogen, a halide group, amine group or an sulphonyl, and is preferably hydrogen. The polyene chain of the cyanine dye may also contain one or more cyclic chemical group that forms bridges between two or more of the carbon atoms of the polyene chain, e.g. by including a —CO— group between two of the carbon atoms of the chain, as in the squaraine dyes, or by including an alkyl bridge. These bridges might serve to increase the chemical or photostability of the dye.

In the formulas I to IV I is a positive integer 1, 2, 3 or 4 giving trimethine, pentamethine, heptamethine or nonamethine cyanine dyes. Preferably, the cyanine dye is a pentamethine or a heptamethine dye with carbon-bridges of 5 and 7 carbon atoms, respectively.

Referring to formula I-IV preferred dyes have altogether 2, 1 or no sulfonic acid moieties attached to the indole rings or benz(e)indole rings. Dyes with a reduced number of sulfonic acid moieties when conjugated to peptides such as the RGD peptide, possess lower blood plasma binding and reduced non-specific binding to background tissue.

Preferred dyes are selected from the group of carbacyanines. And even more preferred are the carbacyanine dyes of the indole type. Preferred dyes of this type are illustrated by formula V:

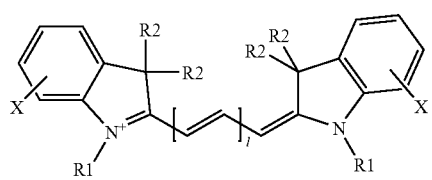

(V)

wherein X is a sulfonic acid moiety or is absent, the R1 groups are the same or different and are substituted or unsubstituted lower alkyls, e.g. C1 to C6 alkyl groups optionally substituted. The alkyl groups are substituted e.g. with carboxy, sulphonic acid, amine, ammonium or ester groups, such as heterocyclic ester groups (e.g. NHS-ester). The R2 groups are lower alkyl groups, such as C1 to C6 alkyls, preferably methyl groups, optionally substituted with e.g. carboxy or sulphonic acid groups. I is an integer of from 1 to 3.

The R1, R2 and X groups are potential linking sites for linking of the cyanine dye to the vector, the R1 and X group being preferred linking sites. In a preferred aspect one R1 group is linked to the vector while the other R1 group is a free lower alkyl group.

Most preferred dyes for use in preparation of contrast agents for use in the method of the invention are the Cy5 mono NHS-ester bis $SO_3$ and the CY7 mono NHS-ester bis $SO_3$ shown below, both comprising a group R1 consisting of an alkyl group substituted with an N-hydroxysuccinimide (NHS) ester which may react with a vector:

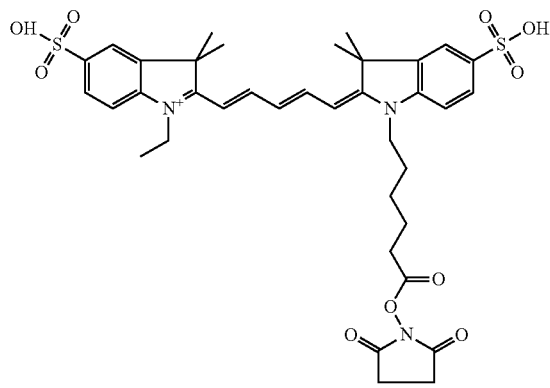

Cy5 mono NHS-ester bis $SO_3$

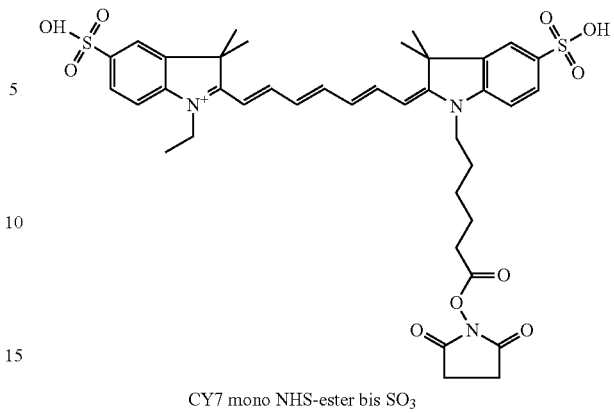

CY7 mono NHS-ester bis $SO_3$

Suitable cyanine dyes have an emission spectrum in the visible or near infra red range, preferably in the range of 500-900 nm, and more preferably in the range of 650-850 nm.

The reporter Z alternatively comprises a fluorescein dye, i.e. fluorescein or derivatives of fluorescein. Fluorescein is a yellow dye which glows in visible light. Fluorescein is typically excited by the 488 nm line of an argon laser, and emission is collected at 530 nm. Fluorescein and its derivatives have relatively high absorptivity, excellent fluorescence quantum yield and good water solubility. The extensive use in the past makes them very well characterised, the availability is very good and they are of low cost.

Formula (VI) shows fluorescein, with the numbering of the different positions of the carbon atoms.

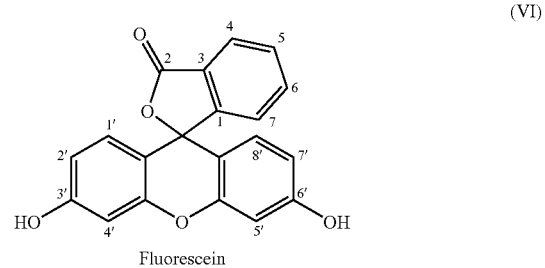

Fluorescein (VI)

Relevant derivatives of fluorescein are e.g. the carboxyfluoresceins, such as the 5-carboxyfluorescein, shown by formula VII, or the 6-carboxyfluorescein.

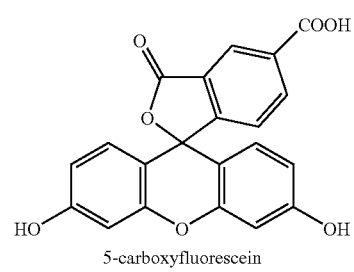

5-carboxyfluorescein (VII)

Another relevant fluorescein derivative is fluorescein isothiocyanate of formula VI:

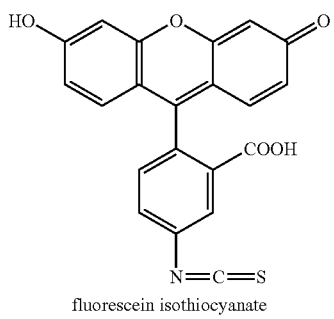

fluorescein isothiocyanate (VIII)

Even more preferred is the use of an activated carboxylate derivative of fluorescein in the preparation of contrast agents for use in the method of the invention, such as an N-hydroxysuccinimide (NHS) ester, called fluorescein NHS ester, shown in formula IX. Succinimidyl esters are excellent reagents since the amide products formed are very stable.

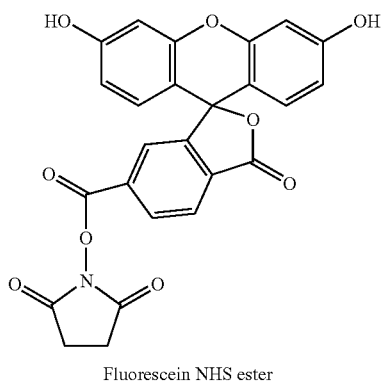

Fluorescein NHS ester (IX)

Preferably, fluorescein is coupled to the vector by amide bond formation with a suitable amino group of the vector. Active esters of fluorescein such as the NHS ester of formula (IX) are commercially available (e.g. Pierce Catalog product no. 46100) and are considered particularly useful When synthesising the contrast agents. Preferred coupling sites for the fluorescein are position 5 and 6.

For the preferred aspect wherein the vector is a peptidic vector comprising the amino acid sequence $X_3$-G-D, the contrast agent can be constrained for example by formation of one or more cyclising bridges in the peptidic vector part. A monocyclic peptide contrast agent can be obtained by formation of a disulfide bond or a thioether bond between amino acids. A peptide-based contrast agent including one cyclising bridge is more specific towards αvβ3, and is more preferred, than a linear peptide. The contrast agents of the invention preferably comprise vectors containing two cyclising bridges between different amino acids of the contrast agents. The term "cyclising bridges" refers to any combination of amino acids or with amino acids and —(CH$_2$)n- or —(CH$_2$)n-C$_6$H$_4$— groups with functional groups which allows for the introduction of a bridge. n represents a positive integer from 1 to 10. Some preferred examples are disulphides, disulphide mimetics such as the —(CH$_2$)$_4$— carba bridge, thioacetal, thioether bridges (cystathione or lanthionine) and bridges containing esters and ethers. Preferably, one bridge forms a disulphide bond and a second bridge comprises a thioether (sulphide) bond. Peptide synthesis and introduction of cyclising bridges can be performed as described in WO01/77145 and WO02/26776.

In a further embodiment the method includes use of a contrast agent defined by formula (Xa)

A-Z (Xa)

wherein A is defined by the formula (Xb)

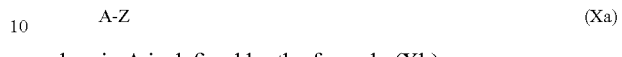

$R_a$—C(=O)—X$_1$—X$_2$—X$_3$-G-D-X$_4$—X$_5$—X$_6$—X$_7$ (Xb)

and Z represents at least one optical imaging reporter, linked to one or more of $X_1$, $X_6$ or $X_7$ of A, optionally via a spacer group, the contrast agent further comprising two cyclising bridges, wherein, $X_3$, G and D are as previously defined; and $R_a$ represents a —(CH$_2$)$_n$— or —(CH$_2$)$_n$—C$_6$H$_4$— group, which forms part of a bridge binding to either of $X_2$, $X_4$ or $X_6$, wherein n represents a positive integer from 1 to 10; and $X_1$ represents a bond or 1, 2, 3, 4 or 5 amino acid residues, wherein one amino acid residue is optionally functionalised with a spacer moiety, and preferably said amino acid residue possesses a functional side-chain such as an acid or amine group preferably selected, from aspartic or glutamic acid, lysine, homolysine, diaminoalkylic acid or diaminopropionic acid; and $X_2$ and $X_4$ represent independently amino acids residues capable of forming a cyclising bridge, such as cysteine or homocysteine residues forming disulphide or thioether bonds, or other amino acid residues capable of forming a cyclising bridge such as aspartic acid and lysine, preferably $X_2$ and $X_4$ represent residues of cysteine or homocysteine; and preferably $X_2$ and $X_4$ form cyclising bridges between each other or with $R_a$ or $X_6$; and $X_5$ represents a hydrophobic amino acid or derivatives thereof, and preferably represents a tyrosine, a phenylalanine, a 3-iodo-tyrosine or a naphthylalanine residue, and more preferably a phenylalanine or a 3-iodo-tyrosine residue; and $X_6$ represents an amino acid residue capable of forming a cyclising bridge, preferably a thiol-containing amino-acid residue, preferably a cysteine or a homocysteine residue; and preferably $X_8$ forms a cyclising bridge with $R_a$, $X_2$ or $X_4$; and $X_7$ represents a spacer or biomodifier moiety or is absent, and is preferably comprising a monodisperse polyethylene glycol (PEG) building block comprising 1 to 10 units of said building block, said biomodifier having the function of modifying the pharmacokinetics and blood clearance rates of said agents. In addition $X_7$ may also represent 1 to 10 amino acid residues preferably comprising glycine, lysine, aspartic acid or serine. $X_7$ may also represent a spacer or biomodifier comprising both amino acid residues and a PEG-like structure, preferably a bis aminoethyl ethylene glycol glycine combination. In a preferred embodiment $X_7$ represents a unit comprised of the monodisperse PEG-like structure, 17-amino-5-oxo-6-aza-3,9,12,15-tetraoxaheptadecanoic acid of formula (XI),

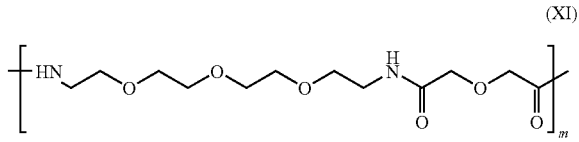

(XI)

wherein m equals an integer from 1 to 10 and where the C-terminal end is an amide or acid moiety. It is found that the biomodifier, $X_7$, modifies the pharmacokinetics and blood clearance rates of the contrast agents. The biomodifier effects less uptake of the contrast agents in tissue i.e. muscle, liver etc. thus giving a better diagnostic image due to less background interference. The secretion is mainly through the kidneys and this represents a further advantage of the biomodifier.

The contrast agents for use in the method of the invention preferably hence comprise a peptidic vector defined by the amino sequence formed by $X_1$, $X_2$, $X_3$, G, D, $X_4$, $X_5$ and $X_6$ of Formula Xb and this peptide constitute a vector having affinity for integrin receptors associated with angiogenesis and wet AMD.

Depending of the placement of the cyclising bridges the contrast agents will comprise "discrete", "nested" or "interlocking" configurations. Preferably the two bridges in each contrast agent are:
Between $R_a$ and $X_6$, and between $X_2$ and $X_4$ (forming a nested configuration);
Between $R_a$ and $X_2$, and $X_4$ and $X_6$ (discrete configuration);
Between $R_a$ and $X_4$, and $X_2$ and $X_6$ (forming an interlocking configuration).

In a preferred embodiment the contrast agent used in the method of the invention comprises one bridge forming a thioether bond and a second bridge forming a disulphide bond.

In a further embodiment the contrast agents of the invention are identified by either of the formulas below. Preparation of contrast agents of formula XIII is described in WO01/77145 and preparation of contrast agents of formula XIII is described in WO 02/26776:

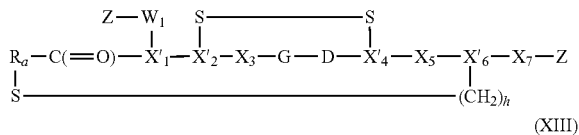

(XII)

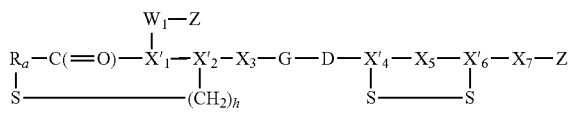

(XIII)

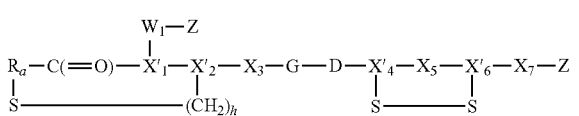

(XIV)

wherein $R_a$, $X_3$, G, D, $X_5$, and $X_7$ are as defined for formula Xb; and wherein
$X'_1$ comprises an amino acid residue with a functional side-chain such as an acid or amine group, the amino acid preferably being selected from aspartic or glutamic acid, homolysine or a diaminoalkylic acid such as lysine or diaminopropionic acid, more preferably aspartic acid or lysine;
$X'_2$, $X'_4$ and $X'_6$ represent amino acid residues capable of forming a disulphide or a thioether bond, such as cysteines or homocysteines, the disulphide and thioether bonds being shown;
$W_1$ is a spacer moiety or is absent, and is preferentially derived from glutaric and/or succinic acid and/or a polyethylenglycol based unit linking the reporter to the peptide. Other representative spacer ($W_1$) elements include structural-type polysaccharides, storage-type polysaccharides, polyamino acids and methyl and ethyl esters thereof, and polypeptides, oligosaccharides and oligonucleotides, which may or may not contain enzyme cleavage sites. The role of the spacer moiety $W_1$ is to distance a relatively bulky reporter from the receptor binding domain of the peptide component;
h is a positive integer 1 or 2;
and wherein at least one of the Z groups is present representing an optical imaging reporter.

The contrast agents preferably include only one Z-group.
The reporter, represented by Z may be linked to $X'_1$, $W_1$, $X_6$ or $X_7$ by amide bond formation. Active esters of the reporter such as the NHS esters are considered particularly useful when synthesising the contrast agents.

In a preferred aspect the contrast agents of formula XII-XIV, or the physiologically acceptable salts thereof, have the following characteristics:
$R_a$ preferably represents —$(CH_2)$—
Further, $X'_1$ represents an amino acid residue with a functional side-chain such as an acid or amine group, the amino acid preferably being selected from aspartic or glutamic acid, lysine, homolysine, diaminoalkylic acid or diaminopropionic acid, more preferably aspartic acid or lysine.
$X'_2$, $X'_4$ and $X'_6$ independently preferably represent a cysteine or a homocysteine residue.
$X_3$ preferably represents arginine.
$X_5$ preferably represents tyrosine, phenylalanine, 3-iodo-tyrosine or naphthylalanine, and more preferably phenylalanine or 3-iodo-tyrosine.
$X_7$ and $W_1$ are defined as for formula XI. Preferably $X_7$ comprises 1-10 units of a monodisperse PEG building block or is absent, and $W_1$ is preferably absent.
Z represents an optical imaging reporter or is absent, provided that the contrast agent comprises at least one optical imaging reporter.

In an even more preferred embodiment the contrast agents used in the method of the invention are of formula XIII (nested) or physiologically acceptable salts thereof, having the characteristics above.

Any of the amino acid residues as defined in formula Xa preferably represent a naturally occurring amino acid. In most cases, it is preferred that the amino acids in the peptidic vector are all in the L-form. However, in some embodiments of the invention one, two, three or more of the amino acids in the peptide are preferably in the D-form. The inclusion of such D-form amino acids can have a significant effect on the serum stability of the contrast agent.

Some of the contrast agents used in the method of the invention comprise high affinity RGD-type vectors. As used herein the term 'high affinity RGD-type vector' refers to contrast agents that have a Ki of <10 nM and preferably <5 nM, in a competitive binding assay for αvβ3 integrin and where the Ki value was determined by competition with the known high affinity ligand echistatin. Methods for carrying out such competition assays are well known in the art.

Some examples of contrast agents of formula Xa for use in the method of the invention are illustrated below.

Contrast agents A, B and C comprise a pentamethine carbacyanine with respectively one, two or four sulfonic acid groups conjugated to an RGD-containing peptide (Lys-Cys-Arg-Gly-Asp-Cys-Phe-Cys). Contrast agents A and B comprise a Cy5 dye, while contrast agent C comprises a Cy5.5 dye:

Contrast agent A:

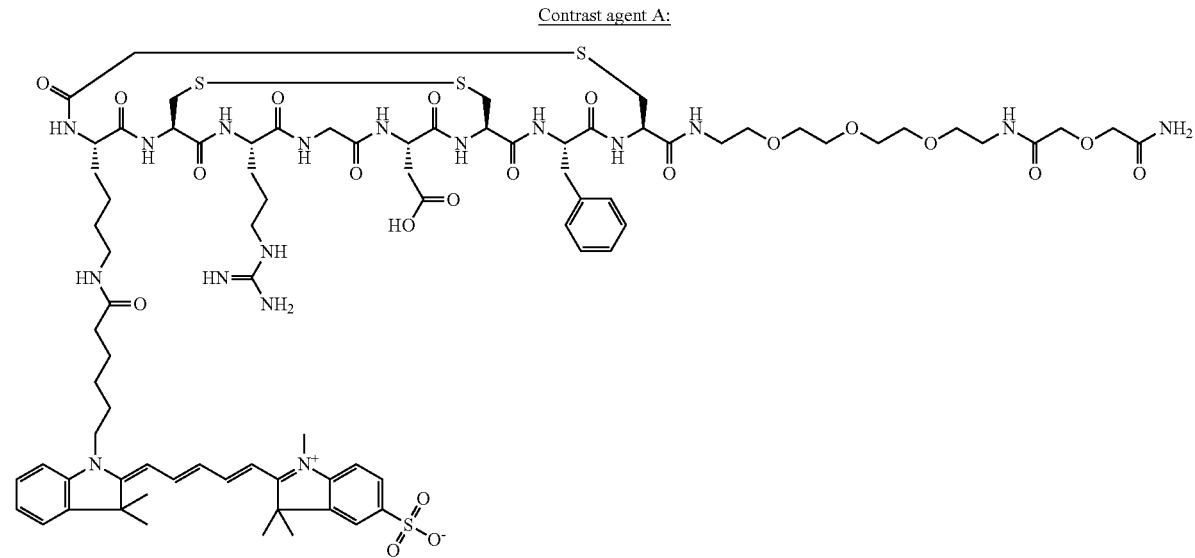

Contrast agent B:

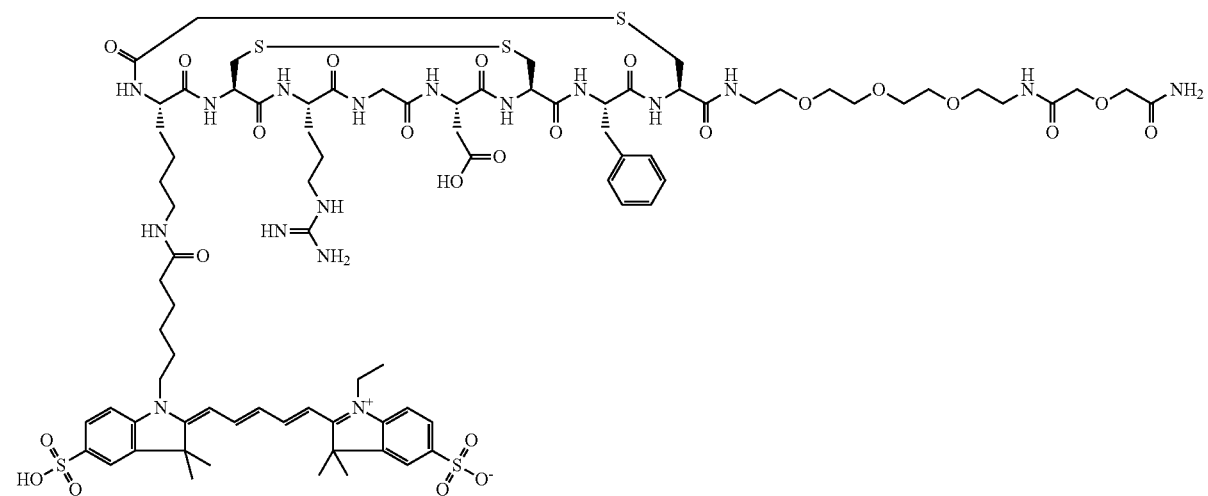

Contrast Agent C:
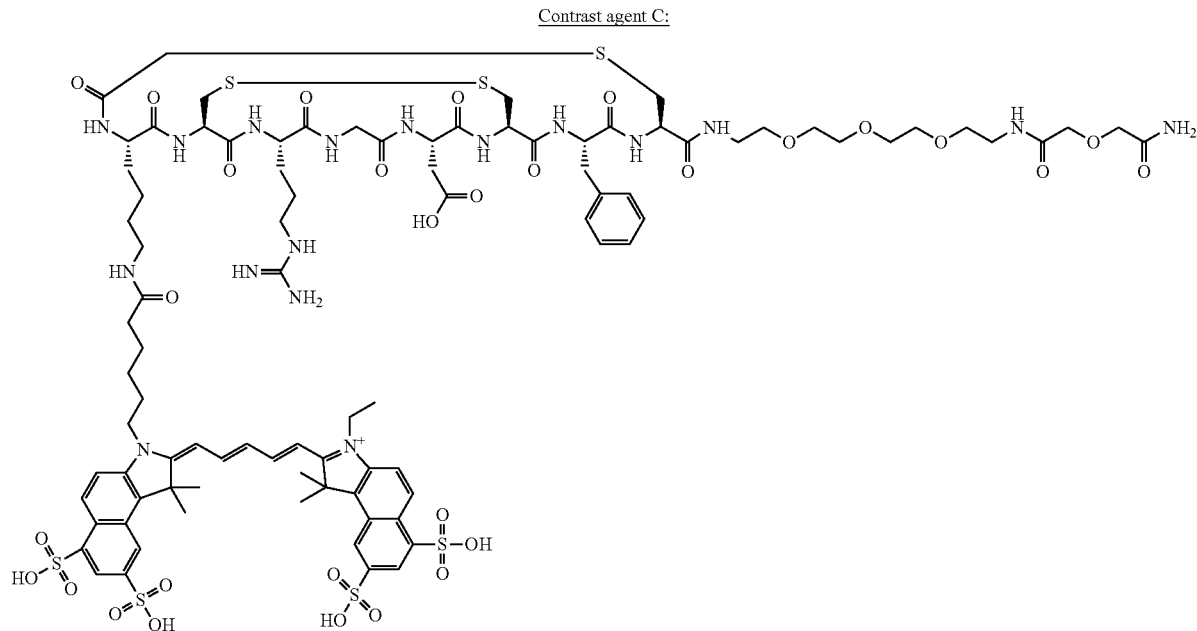
Contrast agent C:
Contrast Agent D:
The peptidic vector D shown below comprising an Asp-Cys-Arg-Gly-Asp-Cys-Phe-Cys peptide can be linked to an optical imaging reporter such as a cyanine dye (e.g. Cy7) by linking the aspartic acid ($X_1$) to an amino-functionalised cyanine dye or by reacting a cyanine dye NHS-ester with the amino-PEG positioned at $X_7$.
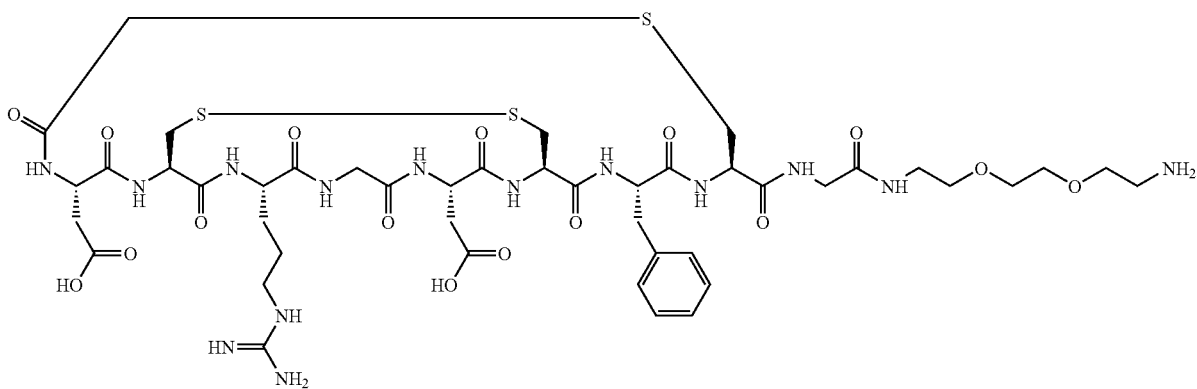

Contrast Agent E:
The contrast agent E comprises an RGD-type peptide (Lys-Cys-Arg-Gly-Asp-Cys-Phe-Cys) linked to two cyanine dye groups (Cy5.5).
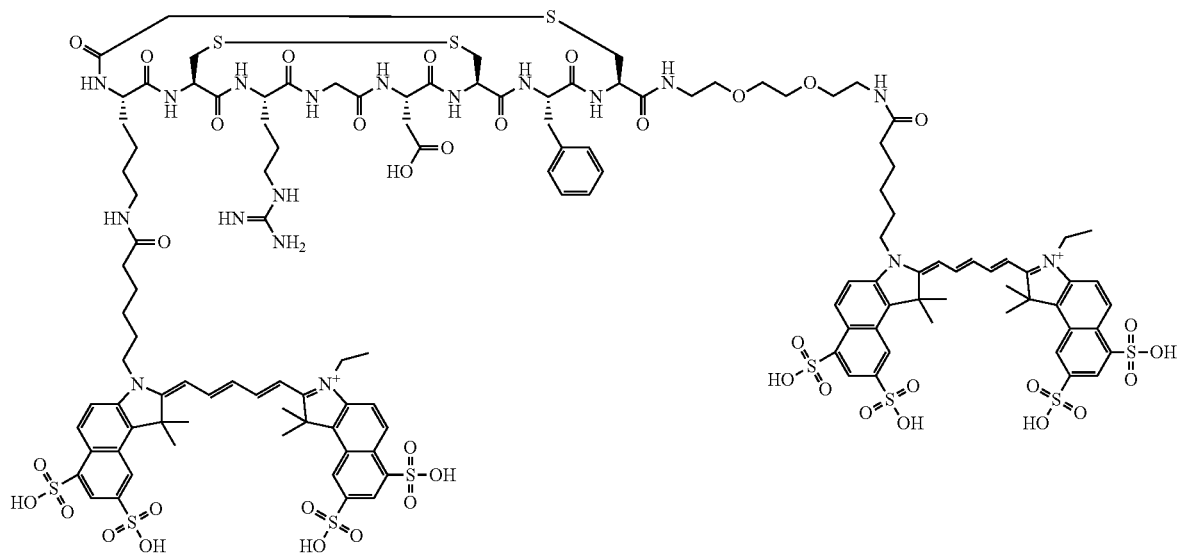
Contrast Agent F:
The contrast agent F comprises a RGD-type peptide (Lys-Asp-Cys-Arg-Gly-Asp-Cys-Phe-Cys-Gly) linked to Cy5.
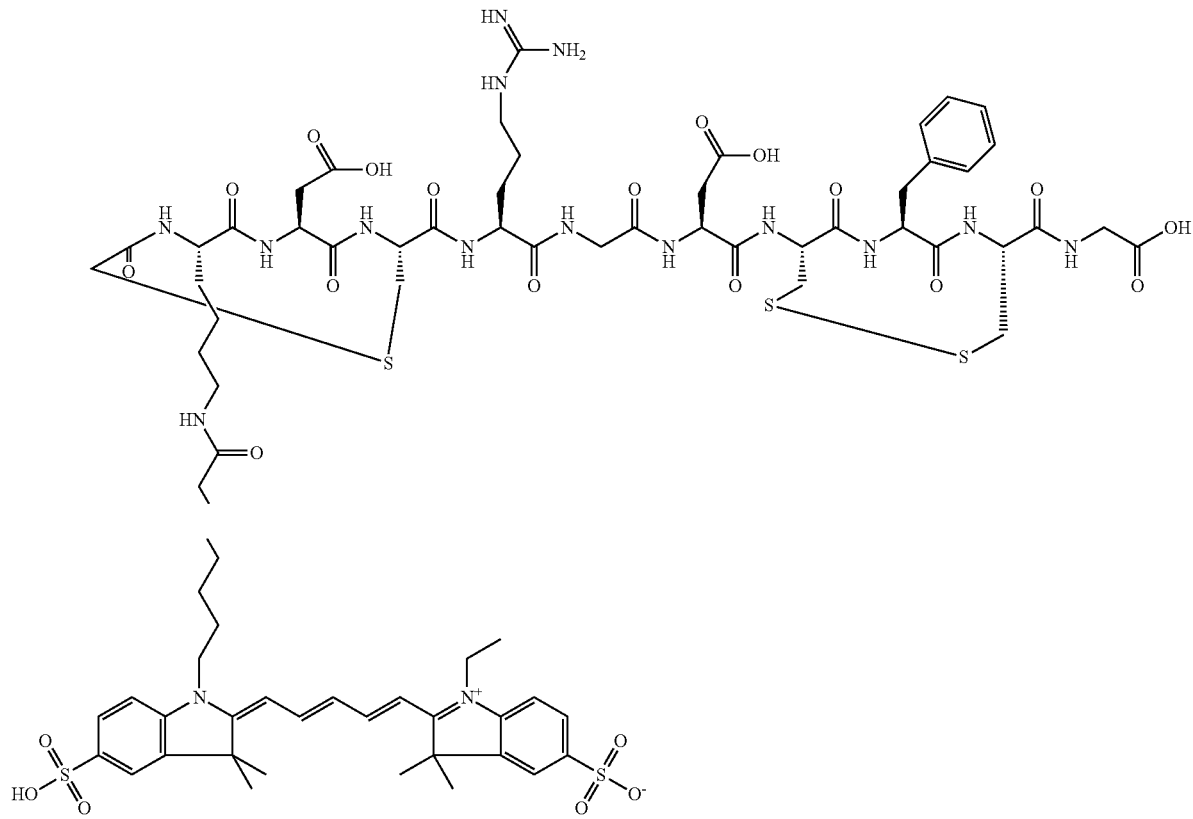

Contrast Agent G:
The monocyclic RGD-type peptide c[-Asp-D-Phe-Lys(Cy5.5)-Arg-Gly-]
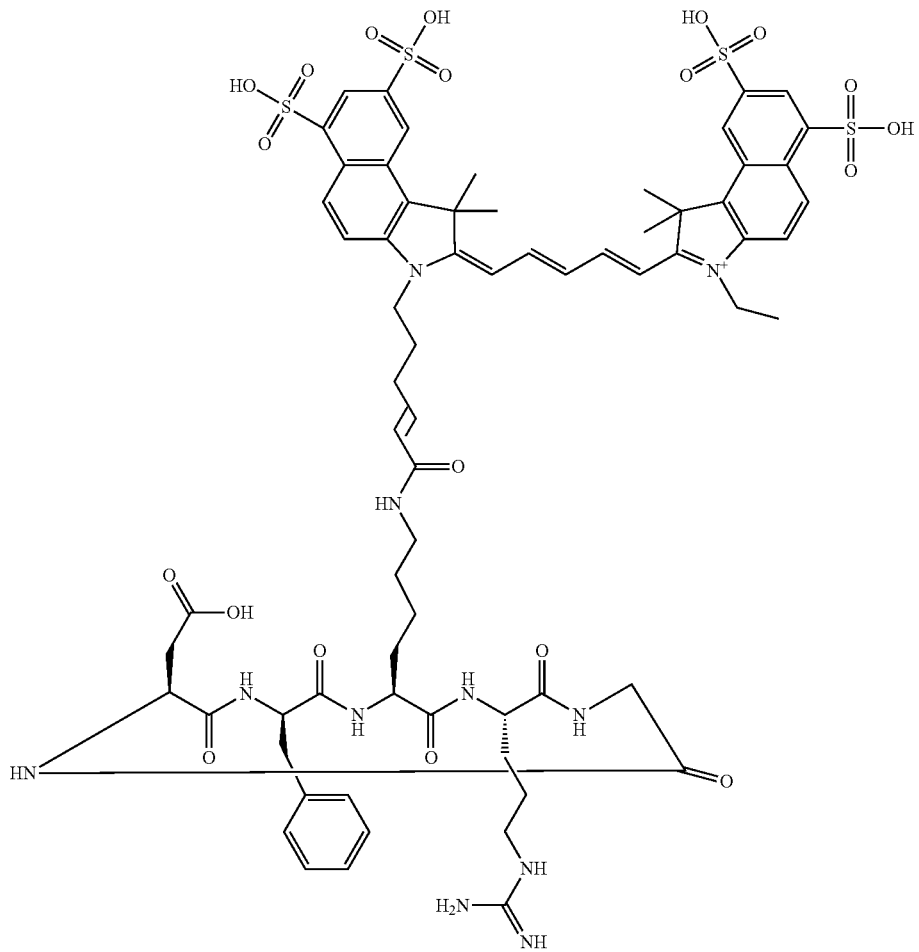
The contrast agents H and I comprise an RGD-type peptide (Lys-Cys-Arg-Gly-Asp-Cys-Phe-Cys) conjugated to fluorescein at different places.
Contrast agent H:
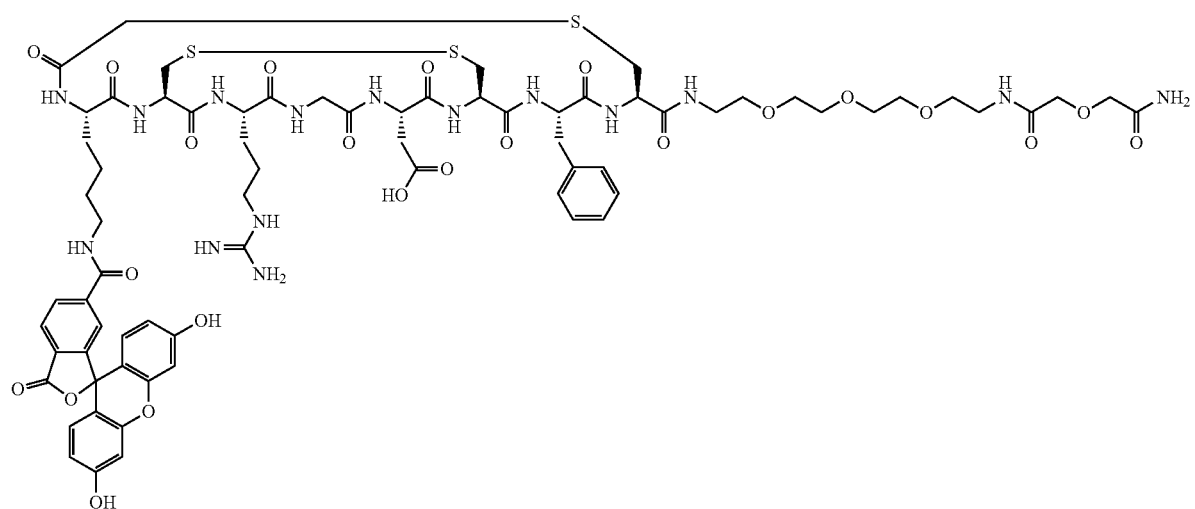

Contrast agent I:
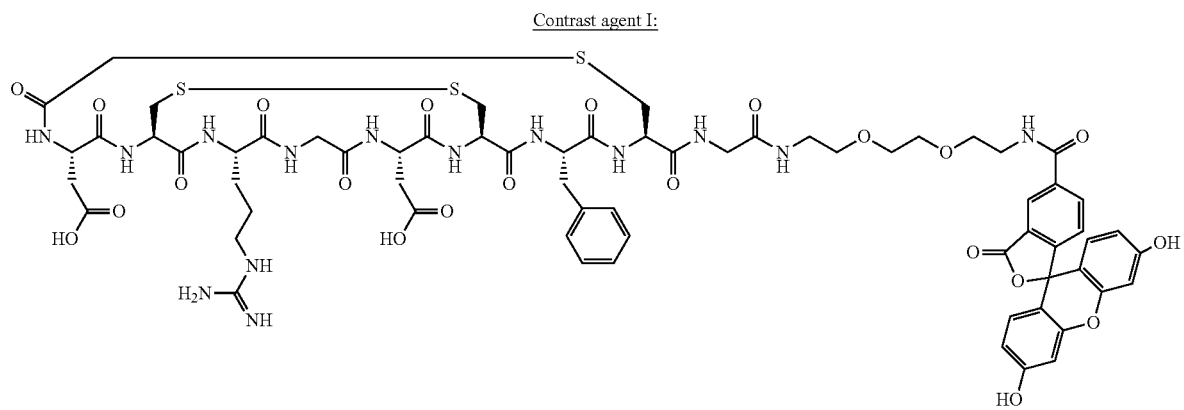
Contrast Agent J:
The contrast agent J comprises an RGD peptide (Lys-Asp-Cys-Arg-Gly-Asp-Cys-Phe-Cys-Gly) linked to fluorescein, forming a "discrete" configuration.
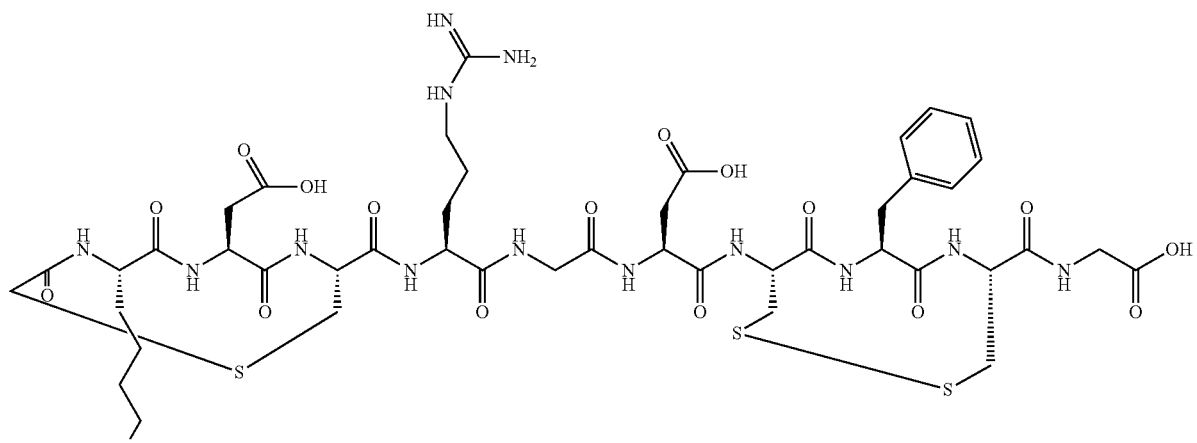
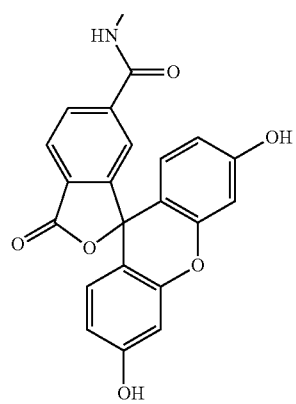

Contrast Agent K:

The contrast agent K comprises an RGD-peptide (Lys-Cys-Arg-Gly-Asp-Cys-Phe-Cys) linked to fluorescein, forming an "interlocking" configuration.

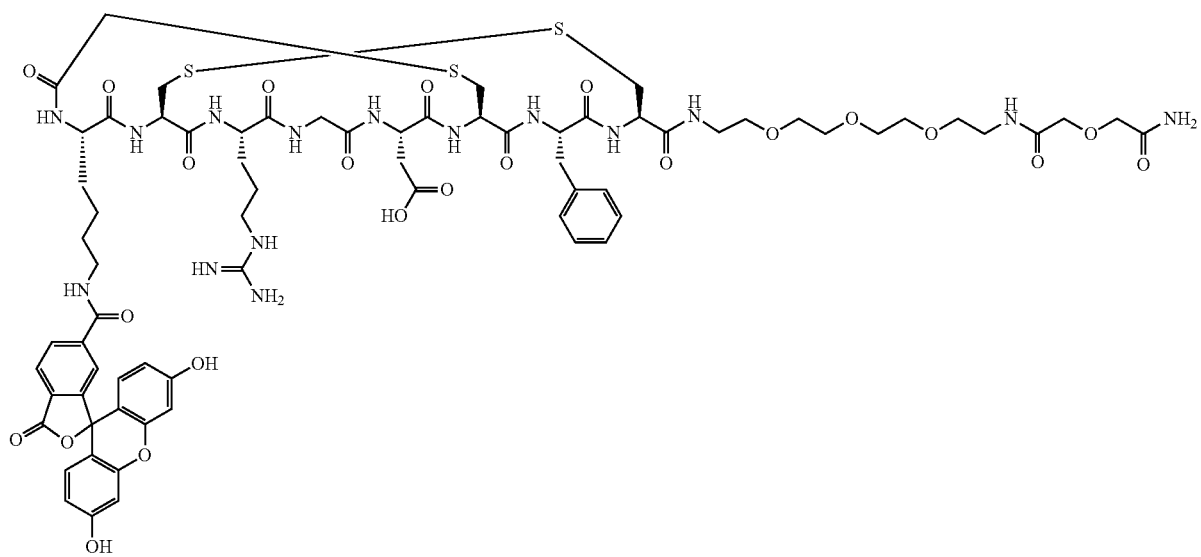

The vectors of the contrast agents described can be synthesized using all the known methods of chemical synthesis but particularly useful is the solid-phase methodology of Merrifield employing an automated peptide synthesizer (J. Am. Chem. Soc., 85: 2149 (1964)).

The coupling of a reporter, such as an active ester of a dye to the vector, can also be carried out automatically yielding an amide bond between the peptide and reporter, or the reporter may be attached to the peptidic vector as described in Examples 1 and 2. The peptidic vectors and peptide contrast agents may be purified using high performance liquid chromatography (HPLC) and characterized by mass spectrometry and analytical HPLC before testing in the in vitro screen.

The present invention will now be further illustrated by way of the following non-limiting examples.

Figure 2:
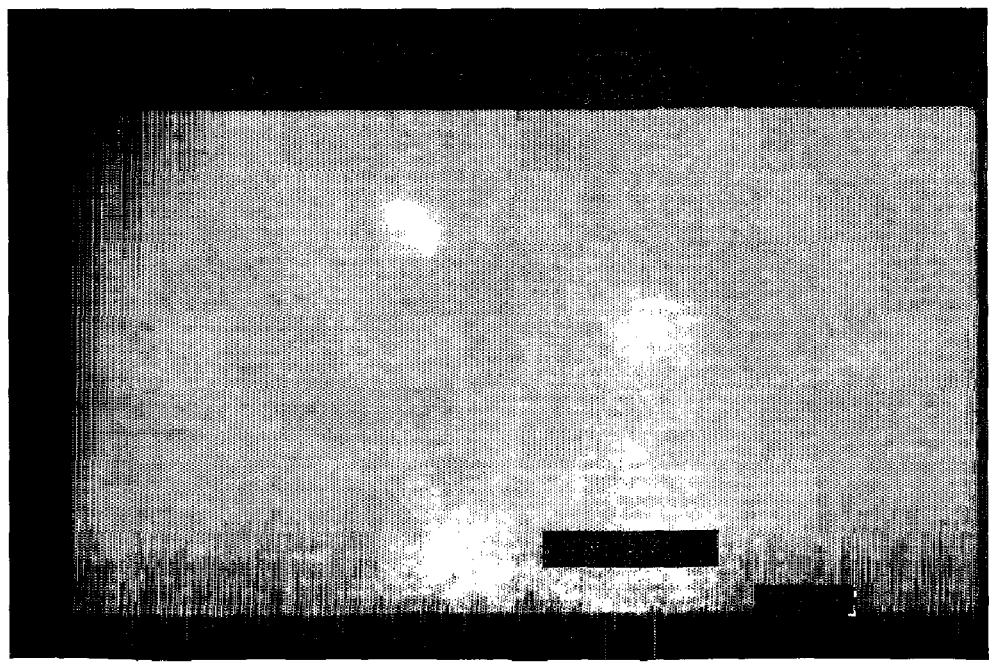
FIG. 2 shows an image of a representative rat eye injected with a negative control.

The FIGS. 1 and 2 refer to example 3 and provide images of eyes of Long Evan rats with induced CNV. FIG. 1 is an image of an eye of a rat injected with contrast agent H and FIG. 2 is an image of an eye injected with a negative control compound.

EXAMPLES

Abbreviations

| | |
|---|---|
| DMF | N,N-Dimethylformamide |
| DMSO | Dimethylsulfoxide |
| Fmoc | N-alpha-(9-fluorenylmethyloxycarbonyl |
| HATU | 2-(1H-7-Azabenzotriazol-1-yl)-1,1,3,3-tetramethyl uronium hexafluorophosphate Methanaminium |
| HPLC | High performance liquid chromatography |
| LC_MS | Liquid chromatography Mass spectroscopy |
| NMM | N-Methylmorpholine |
| tBu | Tert-butyl |
| TFA | Trifluoroactic acid |
| THF | Tetrahydrofuran |

Example 1: Synthesis of Cys2-6; c[CH$_2$CO-Lys(Cy5 bis-SO$_3$)-Cys-Arg-Gly-Asp-Cys-Phe-Cys]-(PEG)n-NH$_2$(n=1) (Contrast agent B)

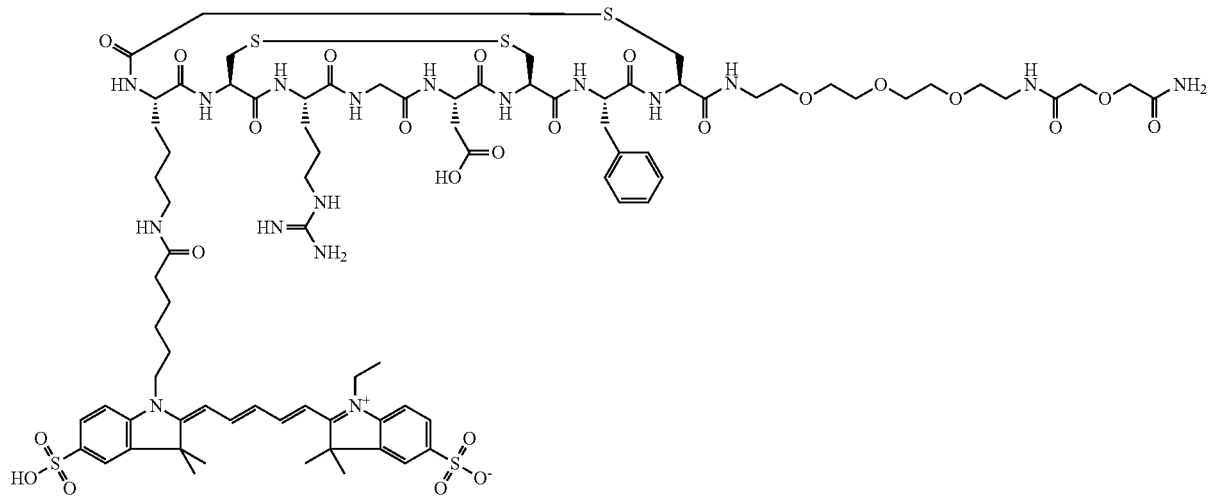

The peptide above was assembled using standard solid phase peptide synthesis methods. The chloroacetylated peptide was cleaved from the solid support and cyclized in solution, first forming the thioether bridge and then the disulfide bridge. The bicyclic peptide (24 mg, 0.02 mmol) was added as a solid to a solution of Cy5 mono NHS-ester bis-SO$_3$ (7.5 mg, 0.01 mmol) in DMF (2 ml), and NMM (0.01 ml, 0.09 mmol) was then added. The reaction was let proceed over night avoid form light. DMF was evaporated under reduced pressure and the crude product was purified by reverse phase preparative chromatography (Vydac C18 column, 218TP1022; solvents: A=water/0.1% TFA and B=CH$_3$CN/0.1% TFA; gradient 10-30% B over 60 min; flow 10 ml/min; detection at 254 nm), affording 6.6 mg (37%) of pure product (analytical HPLC: Phenomenex Luna C18 column, 00G-4252-E0; solvents: A=water/0.1% TFA and B=CH$_3$CN/0.1% TFA; gradient 15-35% B over 20 min; flow 1.0 ml/min; retention time 19.5 min; detection at 214 and 254 nm). Further characterisation was carried out using mass spectrometry, giving m/z value 949.1 [MH$^{2+}$].

Example 2

Synthesis of disulphide [Cys$^{2-6}$]thioether cyclo [CH$_2$CO-Lys(fluorescein)-Cys$^2$-Arg-Gly-Asp-Cys$^6$-Phe-Cys]-PEG-NH, (Contrast agent H)

2 a) Synthesis of 17-(Fmoc-amino)-5-oxo-6-aza-3,9,12,15-tetraoxaheptadecanoic acid This building block is coupled to the solid-phase using Fmoc chemistry. The coupled form of this building block will be referred to in short as PEG.

1,11-Diazido-3,6,9-trioxaundecane

A solution of dry tetraethylene glycol (19.4 g, 0.100 mol) and methanesulphonyl chloride (25.2 g, 0.220 mol) in dry THF (100 ml) was kept under argon and cooled to 0° C. in an ice/water bath. To the flask was added absolution of triethylamine (22.6 g, 0.220 mol) in dry THF (25 ml) dropwise over 45 min. After 1 hr the cooling bath was removed and stirring was continued for 4 hrs. Water (60 ml) was added. To the mixture was added sodium hydrogencarbonate (6 g, to pH 8) and sodium azide (14.3 g, 0.220 mmol), in that order. THF was removed by distillation and the aqueous solution was refluxed for 24 h (two layers formed). The mixture was cooled and ether (100 ml) was added. The aqueous phase was saturated with sodium chloride. The phases were separated and the aqueous phase was extracted with ether (4×50 ml). Combined organic phases were washed with brine (2×50 ml) and dried (MgSO$_4$). Filtration and concentration gave 22.1 g (91%) of yellow oil. The product was used in the next step without further purification.

11-Azido-3,6,9-trioxaundecanamine

To a mechanically, vigorously stirred suspension of 1,11-diazido-3,6,9-trioxaundecane (20.8 g, 0.085 mol) in 5%/o hydrochloric acid (200 ml) was added a solution of triph-

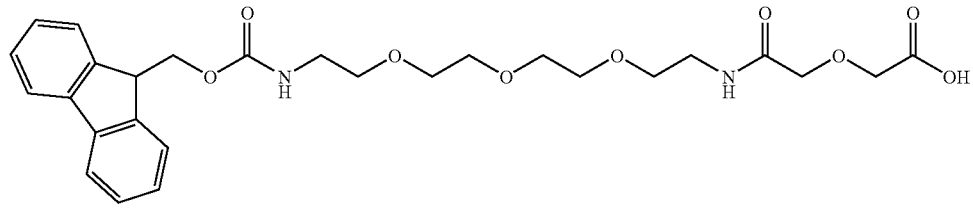

enylphosphine (19.9 g, 0.073 mol) in ether (150 ml) over 3 hrs at room temperature. The reaction mixture was stirred for additional 24 hrs. The phases were separated and the aqueous phase was extracted with dichloromethane (3×40 ml). The aqueous phase was cooled in an ice/water bath and pH was adjusted to ca 12 by addition of KOH. The product was extracted into dichloromethane (5×50 ml). Combined organic phases were dried ($MgSO_4$). Filtration and evaporation gave 14.0 g (88%) of yellow oil. Analysis by MALDI-TOF mass spectroscopy (matrix: α-cyano-4-hydroxycinnamic acid) gave a M+H peak at 219 as expected. Further characterisation using $^1H$ (500 MHz) and $^{13}C$ (125 MHz) NMR spectroscopy verified the structure.

17-Azido-5-oxo-6-aza-3,9,12,15-tetraoxaheptade-canoic acid

To a solution of 11-azido-3,6,9-trioxaundecanamine (10.9 g, 50.0 mmol) in dichloromethane (100 ml) was added diglycolic anhydride (6.38 g, 55.0 mmol). The reaction mixture was stirred overnight. HPLC analysis (column Vydac 218TP54; solvents: A=water/0.1% TFA and B=acetonitrile/0.1% TFA; gradient 4-16% B over 20 min; flow 1.0 ml/min; UV detection at 214 and 284 nm), showed complete conversion of starting material to a product with retention time 18.3 min. The solution was concentrated to give quantitative yield of a yellow syrup. The product was analysed by LC-MS (ES ionisation) giving [MH]+ at 335 as expected. $^1H$ (500 MHz) and $^{13}C$ (125 MHz) NMR spectroscopy was in agreement with structure The product was used in the next step without further purification.

17-Amino-5-oxo-6-aza-3,9,12,15-tetraoxaheptade-canoic acid

A solution of 17-azido-5-oxo-6-aza-3,9,12,15-tetraoxa-heptadecanoic acid (8.36 g, 25.0 mmol) in water (100 ml) was reduced using $H_2(g)$-Pd/C (10%). The reaction was run until LC-MS analysis showed complete conversion of starting material (column Vydac 218TP54; solvents: A=water/0.1% TFA and B=acetonitrile/0.1% TFA; gradient 4-16% B over 20 min; flow 1.0 ml/min; UV detection at 214 and 284 nm, ES ionisation giving M+H at 335 for starting material and 309 for the product). The solution was filtered and used directly in the next step.

17-(Fmoc-amino)-5-oxo-6-aza-3,9,12,15-tetraoxa-heptadecanoic acid

To the aqueous solution of 17-amino-5-oxo-6-aza-3,9,12, 15-tetraoxaheptadecanoic acid from above (corresponding to 25.0 mmol amino acid) was added sodium bicarbonate (5.04 g, 60.0 mmol) and dioxan (40 ml). A solution of Fmoc-chloride (7.11 g, 0.275 mol) in dioxan (40 ml) was added dropwise. The reaction mixture was stirred overnight. Dioxan was evaporated off (rotavapor) and the aqueous phase was extracted with ethyl acetate. The aqueous phase was acidified by addition of hydrochloric acid and precipitated material was extracted into chloroform. The organic phase was dried ($MgSO_4$), filtered and concentrated to give 11.3 g (85%) of a yellow syrup. The structure was confirmed by LC-MS analysis (column Vydac 218TP54; solvents: A=water/0.1% TFA and B=acetonitrile/0.1% TFA; gradient 40-60% B over 20 min; flow 1.0 ml/min; UV detection at 214 and 254 nm, ES ionisation giving M+H at 531 as expected for the product peak at 5.8 minutes). The analysis showed very low content of side products and the material was used without further purification.

2 b) Synthesis of $ClCH_2CO$-Lys-Cys(tBu)-Arg-Gly-Asp-Cys(tBu)-Phe-Cys-PEG-$NH_2$

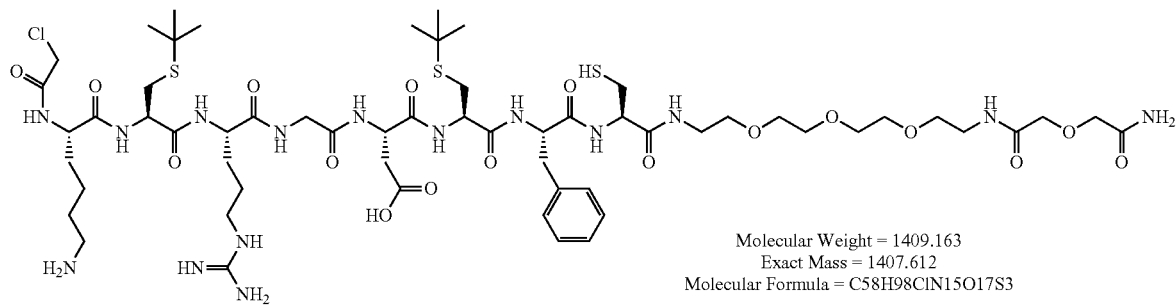

The PEG unit was coupled manually to Rink Amide AM resin, starting on a 0.25 mmol scale, mediated by HATU activation. The remaining peptide was assembled on an ABI 433A automatic peptide synthesiser using 1 mmol amino acid cartridges. The amino acids were pre-activated using HBTU before coupling. N-terminal amine groups were chloroacetylated using a solution of chloroacetic anhydride in DMF for 30 min. The simultaneous removal of peptide and side-chain protecting groups (except tBu) from the resin Was carried out in TFA containing TIS (5%), $H_2O$ (5%) and phenol (2.5%) for two hours. After work-up 322 mg of crude peptide was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 mL/min; detection, UV 214 nm; product retention time, 6.37 min). Further product characterisation was carried out using mass spectrometry: Expected, M+H at 1409. found, at 1415).

2 c) Synthesis of thioether cyclo[CH₂CO-Lys-Cys(tBu)-Arc-Gly-Asp-Cys(tBu)-Phe-Cys]-PEG-NH₂

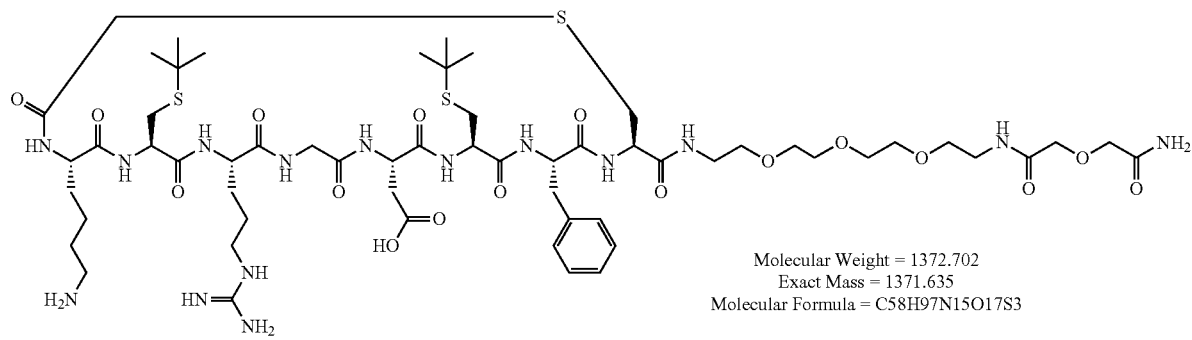

Molecular Weight = 1372.702
Exact Mass = 1371.635
Molecular Formula = C58H97N15O17S3

322 mg of ClCH₂CO-Lys-Cys(tBu)-Arg-Gly-Asp-Cys(tBu)-Phe-Cys-(PEG)n-NH₂ was dissolved in water/acetonitrile. The mixture was adjusted to pH 8 with ammonia solution and stirred for 16 hours. After work-up crude peptide was obtained (Analytical HPLC: Gradient, 5-50% B over 10 min where A=H₂O/0.1% TFA and B=CH₃CN/0.1% TFA; column, Phenomenex Luna 3µ C18 (2) 50×4.6 mm; flow, 2 mL/min; detection, UV 214 nm; product retention time, 6.22 min). Further product characterisation was carried out using mass spectrometry: Expected, M+H at 1373. found, at 1378).

2 d) Synthesis of disulphide [Cys²⁻⁶]thioether cyclo[CH₂CO-Lys-Cys²-Arg-Gly-Asp-Cys⁶-Phe-Cys]-PEG-NH₂

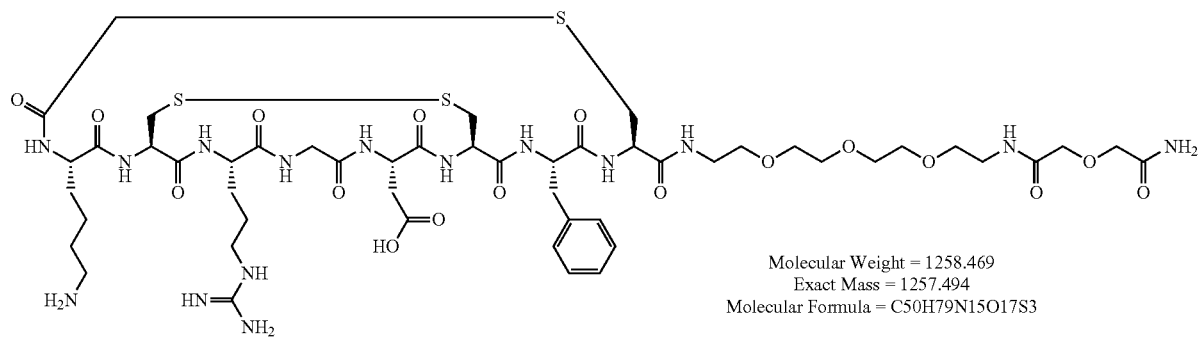

Molecular Weight = 1258.469
Exact Mass = 1257.494
Molecular Formula = C50H79N15O17S3

Thioether cyclo[CH₂CO-Lys-Cys(tBu)-Arg-Gly-Asp-Cys(tBu)-Phe-Cys]-(PEG)n-NH₂ was treated with a solution of anisole (200 µL), DMSO (2 mL) and TFA (100 mL) for 60 min following which the TFA was removed in vacuo and the peptide precipitated by the addition of diethyl ether. Purification by preparative HPLC (Phenomenex Luna 5µ C18 (2) 250×21.20 mm column) of 70 mg crude material was carried out using 0-30% B, where A=H₂O/0.1% TFA and B=CH₃CN/0.1% TFA, over 40 min at a flow rate of 10 mL/min. After lyophilisation 46 mg of pure material was obtained (Analytical HPLC: Gradient, 0-30% B over 10 min where A=H₂O/0.1% TFA and B CH₃CN/0.1% TFA; column, Phenomenex Luna 3µ C18 (2) 50×4.6 mm; flow, 2 mL/min; detection, UV 214 nm; product retention time, 6.80 min). Further product characterisation was carried out using mass spectrometry: Expected, M+H at 1258.5. found, at 1258.8).

2 e) Synthesis of disulfide [Cys$^{2-6}$] thioether cyclo[CH$_2$CO-Lys(fluorescein)-Cys$^2$-Arg-Gly-Asp-Cys$^6$-Phe-Cys]-PEG-NH$_2$

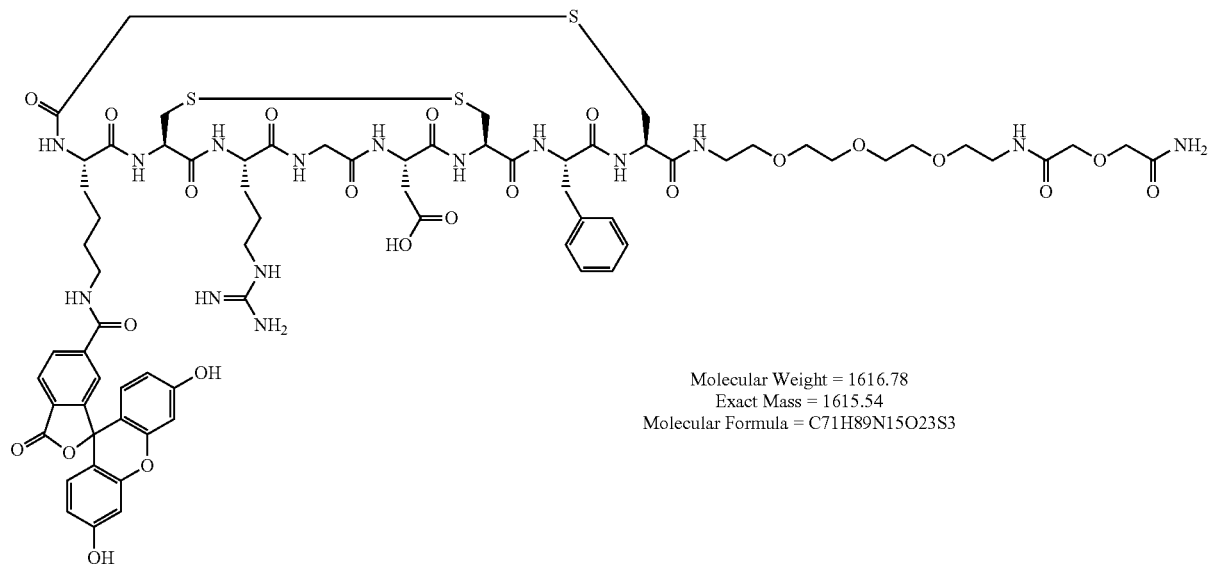

Molecular Weight = 1616.78
Exact Mass = 1615.54
Molecular Formula = C71H89N15O23S3

30 mg of [Cys$^{2-6}$]cyclo[CH$_2$CO-Lys-Cys-Arg-Gly-Asp-Cys-Phe-Cys]-PEG-NH$_2$, 16.2 mg of Fluorescein NHS ester and 4 μL of N-methylmorpholine was dissolved in DMF (3 mL). The mixture was protected against light and stirred over night. Purification by preparative HPLC (Vydac 218TP1022 C18 column) of the reaction mixture was carried out using 20-30% B, where A=H$_2$O/0.1% TFA and B=CH$_3$CN/0.1% TFA, over 40 min at a flow rate of 10 mL/min. After lyophilisation 21.6 mg of pure material was obtained (Analytical HPLC: Gradient, 10-40% B over 10 min where A=H$_2$O/0.1% TFA and B=CH$_3$CN/0.1% TFA; column, Phenomenex Luna 3μ C18 (2) 50×4.6 mm; flow, 2 mL/min; detection, UV 214 nm; product retention time, 7.0 min). Further product characterisation was carried out using mass spectrometry: Expected, M+H at 1616.5. found, at 1616.3).

Example 3

Imaging of CNV

Imaging of choroid neovascularization in rat was performed using the contrast agent from Example 2 (contrast agent H) as an optical imaging contrast agent.

Long-Evans pigmented rats, weighting between 350 g and 400 g, were used for this study. The rats were anesthetized with Ketamine (100 micro-I/100 g) given by intramuscularly injection, and the pupils were dilated with 1% tropicamide eye drop and 0.1% phenylephrine eye drop before the photocoagulation and peptide angiographic examination. Fundus photocoagulation was performed to the right eyes of rats with a diode laser indirect opthalmoscope delivery system under the following condition: Power, 90 mW; wavelength, 810 nm; duration, 0.1 second; and spot size, 75 micro-m. 16 laser burns were delivered around the optic nerve head of each eye. A laser (IRIS Medical, OcuLight™, S/N 25745) was used to make 10 lesions in the Bruch's membrane and choroid. Each lesion was placed approximately 1 mm from the optic nerve head in a radial pattern.

A solution of 0.9% sodium chloride in sterile water was used as the vehicle to prepare dosing solutions. The appropriate amount of the contrast agent was weighed directly into vessel, brought to the appropriate volume, and vortexed as necessary until the contrast agent went into solution. The formulations were stored at room temperature, protected from light, vortexed prior to dosing, and prepared daily.

Negative control: The following compound was used as a negative control. The negative control has the same molecule weight as contrast agent H, but does not comprise the RGD-sequence and does not have affinity for integrins. The negative control compound does not have affinity for receptors associated with angiogenesis.

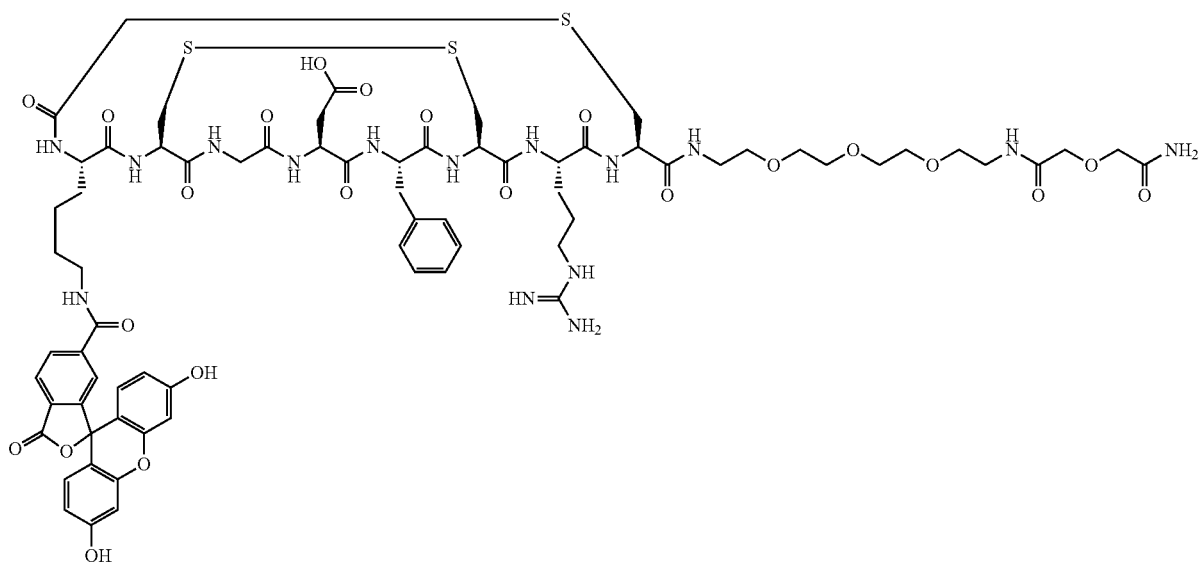

Negative control: [Cys$^{2-6}$]thioether cyclo[CH$_2$CO-Lys(fluorescein)-Cys-Gly-Asp-Phe-Cys-Arg-Cys]-PEG-NH$_2$ The contrast agent solutions were injected intravenously (200 micro-g/kg) to perform molecular angiographies using contrast agent from day 0 post-laser to day 14 post-laser.

Animals:

Long Evans rats (Strain) supplied by (Harlan) were acclimated for a minimum of 1 week prior to dosing. For this study, a total of 27 males and no females were obtained. Housing: Individually, Allentown solid bottom polysulfone cages.

Results:

1 hour post inducing CNV (day 0 post-laser) rats were injected with the contrast agent solutions (contrast agent H or negative control) in doses of 20 μg/kg. Images were taken immediately after administration.

The images show that there is an increased intensity of signal for the induced lesions of the eye of the rat injected with contrast agent H (FIG. 1) compared to the negative control (FIG. 2). Imaging system parameters were identical for the images shown in FIGS. 1 and 2.

---

The invention claimed is:

1. A method of imaging of wet age-related macular degeneration (AMD) of a human or animal body, using a contrast agent comprising a vector attached to an optical imaging reporter wherein the vector has affinity for receptors associated with angiogenesis; further wherein the contrast agent is defined by formula (Xa), $$A\text{-}Z \quad (Xa)$$

wherein A is defined by formula (Xb)

$$R_a\text{—}C(=O)\text{—}X_1\text{—}X_2\text{—}X_3\text{-}G\text{-}D\text{-}X_4\text{—}X_5\text{—}X_6\text{—}X_7 \quad (Xb)$$

and Z represents at least one optical imaging reporter selected from a fluorescein or a cyanine dye linked to one or more of $X_1$, $X_6$ or $X_7$ of A, optionally via a spacer group;
wherein A contains two cyclising bridge;
$X_3$, represents arginine or N-methylarginine;
G represents glycine;
D represents aspartic acid;

$R_a$ represents a —$(CH_2)_n$— or —$(CH_2)_n$—$C_6H_4$— group, which forms part of a bridge to either $X_2$, $X_4$ or $X_6$, wherein n represents a positive integer from 1 to 10;

$X_1$ represents a bond or 1, 2, 3, 4 or 5 amino acid residues, wherein at least one amino acid residue is optionally functionalised with a spacer moiety, or said amino acid residue possesses a functional side-chain selected from an acid or amine group which amino acid residue is selected from the group consisting aspartic or glutamic acid, lysine, homolysine, diaminoalcylic acid and diaminopropionic acid;

$X_2$ and $X_4$ represent independently amino acid residues that forms a cyclising bridge;

$X_5$ represents a hydrophobic amino acid;

$X_6$ represents an amino acid residue that forms a cyclising bridge; and $X_7$ represents a biomodifier moiety comprising a monodispersed polyethylene glycol (PEG) building block comprising 1 to 10 units of said building block.

2. A method as claimed in claim 1 involving administering the contrast agent to said body, irradiating the eye or part of the eye of the human or animal body with light and generating an image of the eye, or part of the eye, to which said contrast agent has distributed.

3. A method as claimed in claim 1 wherein an image is generated from an imaging technique selected from the group consisting of conventional ophthalmoscopy, confocal scanning laser ophthalmoscopy, in-vivo confocal microscopy, time domain and frequency-domain imaging techniques, and a fundus camera.

4. A method as claimed in claim 1 wherein the method further comprises an assessment of the level of angiogenesis in the eye, or part of the eye, of the human or animal body.

5. A method as claimed in claim 1 wherein the vector is selected from the group consisting of
non-peptide mimetics of the RGD tripeptide sequence selected from the group consisting of azacarba, quinalone and indazole compounds, and
peptides comprising the amino acid sequence $X_3$-G-D wherein
$X_3$ represents arginine or N-methylarginine,
G represents glycine,
D represents aspartic acid.

6. A method of generating images of wet AMD of the eye of a human or an animal body by optical imaging, the body being previously administered with a contrast agent comprising a vector attached to an optical imaging reporter, and wherein the vector has affinity for receptors associated with angiogenesis;
further wherein the contrast agent is defined by formula (Xa), $$A\text{-}Z \qquad (Xa)$$

wherein A is defined by formula (Xb)

$$R_a\text{—}C(=O)\text{—}X_1\text{—}X_2\text{—}X_3\text{-}G\text{-}D\text{-}X_4\text{—}X_5\text{—}X_6\text{—}X_7 \qquad (Xb)$$

and Z represents at least one optical imaging reporter selected from a fluorescein or a cyanine dye linked to one or more of $X_1$, $X_6$ or $X_7$ of A, optionally via a spacer group;
wherein A contains two cyclising bridge;
$X_3$, represents arginine or N-methylarginine;
G represents glycine;
D represents aspartic acid;
$R_a$ represents a —$(CH_2)_n$— or —$(CH_2)_n$—$C_6H_4$— group, which forms part of a bridge to either $X_2$, $X_4$ or $X_6$, wherein n represents a positive integer from 1 to 10;
$X_1$ represents a bond or 1, 2, 3, 4 or 5 amino acid residues, wherein at least one amino acid residue is optionally functionalised with a spacer moiety, or said amino acid residue possesses a functional side-chain selected from an acid or amine group which amino acid residue is selected from the group consisting aspartic or glutamic acid, lysine, homolysine, diaminoalcylic acid and diaminopropionic acid;
$X_2$ and $X_4$ represent independently amino acid residues that forms a cyclising bridge;
$X_5$ represents a hydrophobic amino acid;
$X_6$ represents an amino acid residue that forms a cyclising bridge; and
$X_7$ represents a biomodifier moiety comprising a monodispersed polyethylene glycol (PEG) building block comprising 1 to 10 units of said building block.

* * * * *

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: THIOETH
<222> LOCATION: (1)..(8)
<223> OTHER INFORMATION: Disulfid, between position 2 and 6

<400> SEQUENCE: 1

Lys Cys Arg Gly Asp Cys Phe Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: THIOETH
<222> LOCATION: (1)..(8)
<223> OTHER INFORMATION: Disulfid bridge between pos. 2 and 6

<400> SEQUENCE: 2

Asp Cys Arg Gly Asp Cys Phe Cys
```

```
<210> SEQ ID NO 3
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: THIOETH
<222> LOCATION: (1)..(3)
<223> OTHER INFORMATION: Disulfid bridge, between pos. 7 and 9

<400> SEQUENCE: 3

Lys Asp Cys Arg Gly Asp Cys Phe Cys Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(5)
<223> OTHER INFORMATION:

<400> SEQUENCE: 4

Asp Phe Lys Arg Gly
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: THIOETH
<222> LOCATION: (1)..(6)
<223> OTHER INFORMATION: Disulfid bridge, between pos. 2 and 8

<400> SEQUENCE: 5

Lys Cys Arg Gly Asp Cys Phe Cys
1               5
```